(12) United States Patent
Arad

(10) Patent No.: US 7,635,557 B2
(45) Date of Patent: Dec. 22, 2009

(54) ENZYMATIC DIAGNOSTIC TEST FOR SARS AND OTHER VIRAL DISEASES

(75) Inventor: Dorit Arad, Tel Aviv (IL)

(73) Assignee: MND Diagnostic Ltd., Nes Ziona (IL)

( * ) Notice: Subject to any disclaimer, the term of this patent is extended or adjusted under 35 U.S.C. 154(b) by 242 days.

(21) Appl. No.: 10/875,133

(22) Filed: Jun. 23, 2004

(65) Prior Publication Data

US 2005/0048473 A1    Mar. 3, 2005

Related U.S. Application Data

(60) Provisional application No. 60/480,605, filed on Jun. 23, 2003.

(51) Int. Cl.
  C12Q 1/70    (2006.01)
  C12Q 1/00    (2006.01)
  C12Q 1/37    (2006.01)
  G01N 33/53   (2006.01)
  C12N 15/41   (2006.01)

(52) U.S. Cl. .............................. 435/5; 435/4; 435/7.72; 435/23; 435/24

(58) Field of Classification Search .................. None
See application file for complete search history.

(56) References Cited

U.S. PATENT DOCUMENTS

| 4,748,116 | A | | 5/1988 | Simonsson |
|---|---|---|---|---|
| 4,952,493 | A | * | 8/1990 | Kettner et al. ................. 435/5 |
| 5,591,591 | A | | 1/1997 | Bronstein |
| 6,037,137 | A | | 3/2000 | Komoriya |
| 6,127,139 | A | | 10/2000 | Te Kokkele |
| 6,243,980 | B1 | | 6/2001 | Bronstein |
| 6,287,767 | B1 | | 9/2001 | Bronstein |

FOREIGN PATENT DOCUMENTS

WO    WO 2005/017191    2/2005

OTHER PUBLICATIONS

Chiu RW et al, "Automated extraction protocol for quantification of SARS-Coronavirus RNA in serum: an evaluation study" BMC Infectious Diseases 2006, 6:20-26.*

Loens K, et al. "Detection of Rhinoviruses by Tissue Culture and Two Independent Amplification Techniques, Nucleic Acid Sequence-Based Amplification and Reverse Transcription-PCR, in Children with Acute Respiratory Infections during a Winter Season" J Clin Microbiol. Jan. 2006;44(1):166-71.*

Cordingley, et al. Cleavage of Small Peptides in Vitro by Human Rhinovirus 14 3C Protease Expressed in *Escherichia coli*. J. Virol. 1889; 63(12): 5037-5045.*

(Continued)

*Primary Examiner*—Mary E Mosher
*Assistant Examiner*—Stuart W Snyder

(57) ABSTRACT

The present invention is directed towards methods, compositions and kits for testing for a virus in a sample. The methods determine the presence of a viral enzyme by contacting the sample with a peptidal compound capable of being cleaved by the viral enzyme to form peptidal compound fragments. Detection of a peptidal compound fragment confirms the presence of the virus.

12 Claims, 9 Drawing Sheets

Quenched tag

Signal Emitted

OTHER PUBLICATIONS

Hata, et al. A simple purification and fluorescent assay method of the poliovirus 3C protease searching for specific inhibitors. Journal of Virological Methods 84 (2000) 117-126.*

Manafi, et al. Fluorogenic and Chromogenic Substrates Used in Bacterial Diagnostics. Microbiological Reviews, Sep. 1991, vol. 55, No. 3: p. 335-348.*

Wang et al. "Development of A Continous Fluorescence Assay for Rhinovirus 14 3C Protease Using Synthetic Peptides", Antiviral Chemistry & Chemotherapy, 8(4): 303-310, 1997. p. 303, Abstract, p. 304, 1-h Col., p. 306, r-h Col., Paragraph 2, p. 308, r-h Col., Paragraph 3.

Wang et al. "Development of in Vitro Peptide Substrates for Human Rhinovirus-14 2A Protease", Archives of Biochemistry and Biophysics, 356(1): 12-18, 1998. p. 12, Abstract, p. 13, r-h Col., Paragraph 3, p. 15, r-h Col., Paragraph 2.

Makinen, K. et al., J. Gen. Virol. vol. 81, pp. 2783-2789 (2000).

Khan, A. R. et al. "Structural aspects of activation pathways of aspartic protease zymogens and viral 3C protease precursors", Proc. Nat'l. Acad. Sci., vol. 96, No. 20, pp. 10968-10975 (1999).

Rao, M. B. et al., "Molecular and Biotechnological Aspects of Microbial Proteases", Microbiol. and Mol. Biology Rev., vol. 62, No. 3, p. 597-635 (1998).

Corbalenya, A.E. and Snijder, E.J., "Viral cysteine proteinases, Perspectives in Drug Discovery and Design" 6: pp. 64-86 (1996).

Dougherby, W.G. and Semler, B.L., "Expression of virus-encoded protonases: functional and structural similarities with cellular enzymes", Microbial. Rev. 57, pp. 781-822 (1993).

John Ziebuhr et al. "Virus-encoded proteinases and proteolytic processing in the Nidovirales", J. Gen. Vir., vol. 81, pp. 853-879 (2000).

Anand K. et al., Coronavirus Main Protease (3CL$^{pro}$) Structure: Basis of Design of Anti-SARS Drugs Science, vol. 30, pp. 1763-1767 (2003).

Sosnovtsev, S. V., et al., "Cleavage of the feline calicivirus capsid precursor is mediated by a virus-encoded proteinase", J. Virol., vol. 72, pp. 3051-3059 (1998).

Wang, W-K "Detection of SARS-associated Coronavirus in Throat Wash and Saliva in Early Diagnosis" Emerg Infect Dis [serial on the Internet] (Jun. 2004). Available from: http://www.cdc.gov/ncidod/EID/vol10no7/03-1113.htm.

Wang Q.M. et al., "A continuous colorimetric assay for rhinovirus-14 3C protease using peptide p-nitroanilides as substrates" Anal. Biochem. vol. 252, pp. 238-245 (1997).

Basak S. et al. "In vitro elucidation of substrate specificity and bioassay of proprotein convertase 4 using intramolecularly quenched fluorogenic peptides" Biochem. J. vol. 380, pp. 505-514 (2004).

Orr D.C. et al. "Hydrolysis of a series of synthetic peptide substrates by the human rhinovirus 14 3C proteinase, cloned and expressed in *E. coli*", J. Gen. Vir. vol. 70, pp. 2931-2942 (1989).

Rota, Paul A et al. "Characterization of a Novel Coronavirus Associated with Severe Acute Respiratory Syndrome" Science, vol. 300, pp. 1394-1399 (May 30, 2003).

Marra, Marco A. et al., "The Genome Sequence of the SARS-Associated Coronavirus" Science, vol. 300, pp. 1399-1404 (May 30, 2003).

Ksiazek, Thomas G. et al., "A Novel Coronavirus Associated with Severe Respiratory Syndrome" New England Journal of Medicine 348: 20, pp. 1953-1966 (Dec. 2, 2003).

International Search Report for PCT/US2004/019897.

* cited by examiner

Quenched tag          Signal Emitted

| | position Cleavage ↓ | | Cleavage Position Vp4/vp2 | Virus |
|---|---|---|---|---|
| SEQ ID NO:1 | lmlkgapaln | spnveacgys | 69 | HRV14 |
| SEQ ID NO:2 | vlekgiptlq | spsveacgys | 69 | HRV16 |
| SEQ ID NO:3 | lmlkgapaln | spnveacgys | 69 | HRVb |
| SEQ ID NO:4 | lmlktapaln | spnveacgys | 69 | Cxa21 |

```
Sequence Alignment:
HRVb        LMLKGAPALNSPNVEACGYS 20
Cxa21       LMLKTAPALNSPNVEACGYS 20
HRV14       LMLKGAPALNSPNVEACGYS 20
HRV16       VLEKGIPTLQSPSVEACGYS 20
            :: *   *:*:**.*******
Profile     33-K-3P-L2SP2VEACGYS
```

| | | | Vp2/vp3 | |
|---|---|---|---|---|
| SEQ ID NO: 5 | girsksivpq | glptttlpgs | 331 | HRV14 |
| SEQ ID NO: 6 | sgaraktvvq | glpvyvtpgs | 330 | HRV16 |
| SEQ ID NO: 7 | girsksivpq | glptttlpgs | 331 | HRVb |
| SEQ ID NO: 8 | lrnitvpvhq | glptmntpgs | 341 | Cxa21 |

```
HRV16        SGARAKTVV-QGLPVYVTPGS 20
Cxa21        LRNITVPVH-QGLPTMNTPGS 20
HRV14        -GIRSKSIVPQGLPTTTLPGS 20
HRVb         -GIRSKSIVPQGLPTTTLPGS 20
                :  .: ****.   ***
Profile      -------3-QGLP-----PGS
```

| | | | Vp3/vp1 | |
|---|---|---|---|---|
| SEQ ID NO: 9 | fklrlmkdtq | tisqtvalte | 557 | HRV14 |
| SEQ ID NO: 10 | lhkqtgpitq | npveryvdev | 568 | HRV16 |
| SEQ ID NO: 11 | tisqtvalte | glgdeleevi | 567 | HRVb |
| SEQ ID NO: 12 | sqskligrtq | giedlidtai | 581 | Cxa21 |

```
HRV14        FKLRLMKDTQTISQTVALTE---------- 20
HRVb         ----------TISQTVALTEGLGDELEEVI 20
Cxa21        ----------SQSKLIGRTQGIEDLIDTAI 20
HRV16        --------LHKQTGPITQNP-VERYVDEV- 20
                       .  .. . :  :     .
Profile      ------------2--3--2-----------
```

| | | | Vp1/2A | |
|---|---|---|---|---|
| SEQ ID NO: 13 | kkrkgdiksy | glgpryggiy | 856 | HRV14 |
| SEQ ID NO: 14 | irprtnlttv | gpsdmyvhvg | 853 | HRV16 |
| SEQ ID NO: 15 | kkrkgdiksy | glgpryggiy | 856 | HRVb |
| SEQ ID NO: 16 | ltkvdsittf | gfghqnkavy | 879 | Cxa21 |

```
HRV14        KKRKGDIKSYGLGPRYGGIY 20
HRVb         KKRKGDIKSYGLGPRYGGIY 20
Cxa21        LTKVDSITTFGFGHQNKAVY 20
HRV16        IRPRTNLTTVGPSDMYVHVG 20
                .:.:  * .        :
Profile      ------3-2-G-------3-
```

Figure 2(A)

| | position Cleavage ↓ | | Cleavage Position 2A/2B | Virus |
|---|---|---|---|---|
| SEQ ID NO: 17 | rqleciaeeq | glsdyitglg | 1002 | HRV14 |
| SEQ ID NO: 18 | lrhfhcaeeq | gitdyihmlg | 995 | HRV16 |
| SEQ ID NO: 19 | rqleciaeeq | glsdyitglg | 1002 | HRVb |
| SEQ ID NO: 20 | wvyeeeameq | gitsyieslg | 1028 | Cxa21 |

```
Sequence Alignment:
HRV16           LRHFHCAEEQGITDYIHMLG 20
Cxa21           WVYEEEAMEQGITSYIESLG 20
HRV14           RQLECIAEEQGLSDYITGLG 20
HRVb            RQLECIAEEQGLSDYITGLG 20
                 * ***::.**   **
Profile         ------A-EQG32-YI--LG
```

| | | | 2B/2C | |
|---|---|---|---|---|
| SEQ ID NO: 21 | hfqvpyierq | andgwfrkfn | 1099 | HRV14 |
| SEQ ID NO: 22 | wtqltyihke | sdswlkkfte | 1090 | HRV16 |
| SEQ ID NO: 23 | hfqvpyierq | andgwfrkfn | 1099 | HRVb |
| SEQ ID NO: 24 | lleipyvmrq | gdgwmkkfte | 1125 | Cxa21 |

```
HRV14           HFQVPYIERQANDGWFRKFN- 20
HRVb            HFQVPYIERQANDGWFRKFN- 20
Cxa21           LLEIPYVMRQG-DGWMKKFTE 20
HRV16           WTQLTYIHKES-DSWLKKFTE 20
                 ::.*:  ::. *.*::**.
Profile         ---3-Y3-5---D-W-5KF2-
```

| | | | 2C/3A | |
|---|---|---|---|---|
| SEQ ID NO: 25 | itdsletlfq | gpvykdleid | 1429 | HRV14 |
| SEQ ID NO: 26 | vvdvmsaifq | gpismdkppp | 1412 | HRV16 |
| SEQ ID NO: 27 | itdsletlfq | gpvykdleid | 1429 | HRVb |
| SEQ ID NO: 28 | igncmealfq | gplrykdlki | 1453 | Cxa21 |

```
HRV14           ITDSLETLFQGPV-YKDLEID 20
HRVb            ITDSLETLFQGPV-YKDLEID 20
Cxa21           IGNCMEALFQGPLRYKDLKI- 20
HRV16           VVDVMSAIFQGPISMDKPPP- 20
                :  : :.::****:  ..  .
Profile         3---3--3FQGP3----3---
```

Figure 2(B)

|  |  | position Cleavage ↓ | Cleavage Position | Virus |
| --- | --- | --- | --- | --- |
| SEQ ID NO: 29 |  | viyklfaqtq | gpysgnpphn | 1514 | HRV14 |
| SEQ ID NO: 30 |  | iiyklfcslq | gpysgepkpk | 1489 | HRV16 |
| SEQ ID NO: 31 |  | viyklfaqtq | gpysgnpphn | 1514 | HRVb |
| SEQ ID NO: 32 |  | vmyklfagqq | gaytglpnkk | 1541 | Cxa21 |

```
Sequence Alignment:
HRV14         VIYKLFAQTQGPYSGNPPHN 20
HRVb          VIYKLFAQTQGPYSGNPPHN 20
HRV16         IIYKLFCSLQGPYSGEPKPK 20
Cxa21         VMYKLFAGQQGAYTGLPNKK 20
              ::****. **.*:*  *   :
Profile       33YKLF---QG3Y2G-P---
```

|  |  | | | |
| --- | --- | --- | --- | --- |
| SEQ ID NO: 33 |  | aptlrpvvvq | gpntefalsl | 1537 | HRV14 |
| SEQ ID NO: 34 |  | kvperrvvaq | gpeeefgmsi | 1510 | HRV16 |
| SEQ ID NO: 35 |  | aptlrpvvvq | gpntefalsl | 1537 | HRVb |
| SEQ ID NO: 36 |  | vptirvakvq | gpgfdyavam | 1563 | Cxa21 |

```
HRV14         -APTLRPVVVQGPNTEFALSL 20
HRVb          -APTLRPVVVQGPNTEFALSL 20
HRV16         KVPERR-VVAQGPEEEFGMSI 20
Cxa21         -VPTIRVAKVQGPGFDYAVAM 20
              .*  *  .*** ::.:::
Profile       -3P--RP3-3QGP--4--3-3
```

|  |  | | | |
| --- | --- | --- | --- | --- |
| SEQ ID NO: 37 |  | lkkqyfvekq | gqviarhkvr | 1719 | HRV14 |
| SEQ ID NO: 38 |  | llrsyfteqq | gqiqiskhvk | 1693 | HRV16 |
| SEQ ID NO: 39 |  | lkkqyfvekq | gqviarhkvr | 1719 | HRVb |
| SEQ ID NO: 40 |  | lkrsyftqnq | geiqwmrssk | 1746 | Cxa21 |

```
HRV16         LLRSYFTEQQGQIQISKHVK 20
Cxa21         LKRSYFTQNQGEIQWMRSSK 20
HRV14         LKKQYFVEKQGQVIARHKVR 20
HRVb          LKKQYFVEKQGQVIARHKVR 20
              * :.**.::**::    :  :
Profile       L-52YF---QG-3------5
``` profile key :

| Group | Symbol | Amino acids |
| --- | --- | --- |
| Aromatic | 1 | F Y W H |
| H-bonds | 2 | Q N S T C H |
| Hydrophobic | 3 | A L I V P C M |
| Acid | 4 | D E |
| alkaly | 5 | K R Q N H |

Figure 2(C)

```
HRV14_2C_3A      -ITDSLETLFQ    GPV-YKDLEID-  20
HRVb_2C_3A       -ITDSLETLFQ    GPV-YKDLEID-  20
Cxa21_2C_3A      -IGNCMEALFQ    GPLRYKDLKI--  20
HRV16_2C_3A      -VVDVMSAIFQ    GPISMDKPPP--  20
HRV14_3A_3B      -VIYKLFAQTQ    GPYS-GNPPHN-  20
HRVb_3A_3B       -VIYKLFAQTQ    GPYS-GNPPHN-  20
Cxa21_3A_3B      -VMYKLFAGQQ    GAYT-GLPNKK-  20
HRV16_3A_3B      -IIYKLFCSLQ    GPYS-GEPKPK-  20
HRV14_3B_3C      -APTLRPVVVQ    GPN--TEFALSL  20
HRVb_3B_3C       -APTLRPVVVQ    GPN--TEFALSL  20
Cxa21_3B_3C      -VPTIRVAKVQ    GPG--FDYAVAM  20
HRV16_3B_3C      KVPERR-VVAQ    GPE--EEFGMSI  20
                           *      *
```

| Group % | * | V 50 | 3 75 | | 3 75 | 3 75 | 3 75 | Q 100 | G 100 | P 92 | | | | 4 67 | | | | |
|---|---|---|---|---|---|---|---|---|---|---|---|---|---|---|---|---|---|---|
| | | I 30 | | | | | | | | A 8 | | | | | | | | |
| | | A 20 | | | | | | | | | | | | | | | | |
| consensus | | 3 | | | 3 | 3 | 3 | Q | G | P | | | | 4 | | | | |

Figure 2(D)

|  |  |  |  | Cleavage Position | Virus |
|---|---|---|---|---|---|
|  | SEQ ID NO: 41 | reltrelngg | avtryvdnnf | 180 | SARS |
|  | SEQ ID NO: 42 | mskinkygle | vkpllyvdqy | 246 | BCov |
|  | SEQ ID NO: 43 | dvvfgkrggg | nvtytdqylc | 111 | HCov |

```
Sequence Alignment:
BCOV        MSKINKYGLEVKP-LLYVDQY-- 20
HCOV        --DV-VFGKRGGGNVTYTDQYLC 20
SARS        -REL-TRELNGGAVTRYVDNNF- 20
                .:      .       *.*:
Profile     ---3------------Y-D2---
```

|  |  |  |  |  |  |
|---|---|---|---|---|---|
|  | SEQ ID NO: 44 | tnnvfrlkgg | apikgvtfge | 818 | SARS |
|  | SEQ ID NO: 45 | ldqawrvpca | grrvtfkeqp | 851 | BCov |
|  | SEQ ID NO: 46 | lpvaftkaag | gkvsfsddve | 897 | HCov |

```
BCOV        LDQAWRVPCAG--RRVTFKEQP- 20
SARS        TNNVFRLKGGAPIKGVTFGE--- 20
HCOV        LPVAFTKAAGG---KVSFSDDVE 20
                .:     ...    *:*  :
Profile     ---31----------V2F-4---
```

|  |  |  |  |  |  |
|---|---|---|---|---|---|
|  | SEQ ID NO: 47 | ittkislkgg | kivstcfklm | 2740 | SARS |
|  | SEQ ID NO: 48 | lttpfslkgg | avfsyfvyvc | 2750 | BCov |
|  | SEQ ID NO: 49 | atsivakqga | gdaghsltwl | 2484 | HCov |

```
SARS        ITTKISLKGGKIVSTCFKLM 20
BCOV        LTTPFSLKGGAVFSYFVYVC 20
HCOV        ATSIVAKQGAGDAGHSLTWL 20
            *:  .:  :*.    .   .
Profile     3T2----5G----------3
```

|  |  |  |  | 4-5 |  |
|---|---|---|---|---|---|
|  | SEQ ID NO: 50 | qtsitsavlq | sgfrkmafps | 3240 | SARS |
|  | SEQ ID NO: 51 | tasvstsflq | sgivkmvnpt | 3246 | BCov |
|  | SEQ ID NO: 52 | ptvsygstlq | aglrkmaqps | 2965 | HCov |

```
SARS        QTSITSAVLQSGFRKMAFPS 20
HCOV        PTVSYGSTLQAGLRKMAQPS 20
BCOV        TASVSTSFLQSGIVKMVNPT 20
               :    :**:*: **. *:
Profile     --------LQ-G--KM3-P2
```

Figure 3(A)

| | | | Cleavage Position 3CL | Virus |
|---|---|---|---|---|
| SEQ ID NO: 53 | vrqcsgvtfq | gkfkkivkgt | 3546 | SARS |
| SEQ ID NO: 54 | yqqlagiklq | skrtrlvkgi | 3549 | BCov |
| SEQ ID NO: 55 | vkqmfgvnlq | sgkttsmfks | 3267 | HCov |

```
Sequence Alignment:
SARS            VRQCSGVTFQ-GKFKKIVKGT 20
BCOV            YQQLAGIKLQ-SKRTRLVKGI 20
HCOV            VKQMFGVNLQSGKTTSMFKS- 20
                 :*  *:.:* .* . :.*.
Profile         -5Q3-G3---Q-K---3-K--
```

| | | | | |
|---|---|---|---|---|
| SEQ ID NO: 56 | kpcikvatvq | skmsdvkcts | 3836 | SARS |
| SEQ ID NO: 57 | vpiievsqfq | skltdvkcan | 3836 | BCov |
| SEQ ID NO: 58 | prtikvstvq | skltdlkctn | 3546 | HCov |

```
BCOV            VP-IIEVSQFQSKLTDVKCAN 20
HCOV            -PRTIKVSTVQSKLTDLKCTN 20
SARS            KP-CIKVATVQSKMSDVKCTS 20
                 *  *:*: .***::*:**:.
Profile         -P--I-V-2-QSK32D3KC-2
```

| | | | | |
|---|---|---|---|---|
| SEQ ID NO: 59 | emldnratlq | aiasefsslp | 3919 | SARS |
| SEQ ID NO: 60 | dyakdntvlq | alqsefvnma | 3925 | BCov |
| SEQ ID NO: 61 | syfendsilq | svassfvgmp | 3629 | HCov |

```
BCOV            DYAKDNTVLQALQSEFVNMA 20
HCOV            SYFENDSILQSVASSFVGMP 20
SARS            EMLDNRATLQAIASEFSSLP 20
                .  .: : **:: *.* .:.
Profile         --------LQ-3-S-F--33
```

| | | | | |
|---|---|---|---|---|
| SEQ ID NO: 62 | lransavklq | nnelspvalr | 4117 | SARS |
| SEQ ID NO: 63 | hnevsatvlq | nnelmpaklk | 4122 | BCov |
| SEQ ID NO: 64 | ltcervvklq | nneimpgkmk | 3824 | HCov |

```
BCOV            HNEVSATVLQNNELMPAKLK 20
HCOV            LTCERVVKLQNNEIMPGKMK 20
SARS            LRANSAVKLQNNELSPVALR 20
                     .. *****: *  ::
Profile         -----3--LQNNE3-P--35
```

Figure 3(B)

|  |  |  | Cleavage Position |  |
|---|---|---|---|---|
| SEQ ID NO: 65 | gslaatvrlq | agnatevpan | 4230 | SARS |
| SEQ ID NO: 66 | gtisstvrlq | agtateyasn | 4232 | BCov |
| SEQ ID NO: 67 | gyigatvrlq | agkqtefvsn | 3933 | HCov |

```
Sequence Alignment:
BCOV          GTISSTVRLQAGTATEYASN 20
HCOV          GYIGATVRLQAGKQTEFVSN 20
SARS          GSLAATVRLQAGNATEVPAN 20
              * :.:*******. **  :*
Profile       G-3--TVRLQAG--TE-3-N
```

|  |  |  |  |  |
|---|---|---|---|---|
| SEQ ID NO: 68 | cdqlreplmq | sadastflnr | 4369 | SARS |
| SEQ ID NO: 69 | scvstdttvq | skdtnflnrv | 4369 | BCov |
| SEQ ID NO: 70 | gctcdrtaiq | sfdnsylnrv | 4068 | HCov |

```
BCOV          SC-VSTDTTVQSKDTN-FLNRV 20
HCOV          GC-TCDRTAIQSFDNS-YLNRV 20
SARS          -CDQLREPLMQSADASTFLNR- 20
               *       .:** *  .:***
Profile       -C-------3QS-D-2--LNR-
```

|  |  |  |  |  |
|---|---|---|---|---|
| SEQ ID NO: 71 | amytphtvlq | avgacvlcns | 5301 | SARS |
| SEQ ID NO: 72 | nmylrsavmq | svgacvvcss | 5297 | BCov |
| SEQ ID NO: 73 | smyekstvlq | aaglcvvcgs | 4995 | HCov |

```
SARS          AMYTPHTVLQAVGACVLCNS 20
HCOV          SMYEKSTVLQAAGLCVVCGS 20
BCOV          NMYLRSAVMQSVGACVVCSS 20
              **   :*:*:.* **:*.*
Profile       -MY-2-V3Q-3G3CV3C-S
```

|  |  |  |  |  |
|---|---|---|---|---|
| SEQ ID NO: 74 | iprrnvatlq | aenvtglfkd | 5902 | SARS |
| SEQ ID NO: 75 | vpqavetrvq | cstnlfkdcs | 5900 | BCov |
| SEQ ID NO: 76 | ffeitmtdlq | sesscglfkd | 5592 | HCov |

```
SARS          IPRRNVATLQAENVTGLFKD-- 20
HCOV          FFEITMTDLQSESSCGLFKD-- 20
BCOV          VPQAVETRVQCS--TNLFKDCS 20
              . .  : :*..  .****
Profile       --------3Q----2-LFKD--
```

Figure 3(C)

| | | | Cleavage Position | Virus |
|---|---|---|---|---|
| SEQ ID NO: 77 | nlwntftrlq | slenvaynvv | 6429 | SARS |
| SEQ ID NO: 78 | nlwntftklq | slenvvynlv | 6421 | BCov |
| SEQ ID NO: 79 | wqtftevnlq | gleniafnvv | 6110 | HCov |

```
Sequence Alignment:
SARS        NLWNTFTR--LQSLENVAYNVV 20
BCOV        NLWNTFTK--LQSLENVVYNLV 20
HCOV        --WQTFTEVNLQGLENIAFNVV 20
            . *:***.  **.***::*:*
Profile     --W2TFT---LQ-LEN33-N3V
```

| | | | | |
|---|---|---|---|---|
| SEQ ID NO: 80 | hvetfypklq | asqawqpgva | 6775 | SARS |
| SEQ ID NO: 81 | kvmtfyprlq | aasdwkpgys | 6795 | BCov |
| SEQ ID NO: 82 | avatfypqlq | saewkcgysm | 6458 | HCov |

```
BCOV        KVMTFYPRLQAASDWKPGYS- 20
HCOV        AVATFYPQLQSA-EWKCGYSM 20
SARS        HVETFYPKLQASQAWQPGVA- 20
            *  ****:**::    *:  * :
Profile     -V-TFYP-LQ----W--G---
``` profile key :

| Group | Symbol | Amino acids |
|---|---|---|
| Aromatic | 1 | F Y W H |
| H-bonds | 2 | Q N S T C H |
| Hydrophobic | 3 | A L I V P C M |
| Acid | 4 | D E |
| alkaly | 5 | K R Q N |

```
QTSITSAVLQSGFRKMAFPS 20
VRQCSGVTFQ-GKFKKIVKG 20
KPCIKVATVQSKMSDVKCTS 20
EMLDNRATLQAIASEFSSLP 20
LRANSAVKLQNNELSPVALR 20
GSLAATVRLQAGNATEVPAN 20
CDQLREPLMQSADASTFLNR-
AMYTPHTVLQAVGACVLCNS 20
IPRRNVATLQAENVTGLFKD-20
WNTFTR--LQSLENVAYNVV 20

XXLQA(S)GXX
```

Figure 3(D)

ENZYMATIC DIAGNOSTIC TEST FOR SARS AND OTHER VIRAL DISEASES

RELATED APPLICATIONS

This application claims priority to U.S. Provisional Patent Application No. 60/480,605, filed Jun. 23, 2003, the entire content of which is fully incorporated herein by reference.

TECHNICAL FIELD OF THE INVENTION

The present invention provides a method, reagents and a kit for the detection of a virus in a test sample. The method involves the detection of an enzyme that is encoded by a viral nucleic acid during the replication of the virus. In one embodiment, the invention provides a method for detection of the Severe Acute Respiratory Syndrome (SARS) virus in a sample.

BACKGROUND

There is a continuing need for rapid sensitive methods for the detection of viral diseases. Rapid detection and identification of viral pathogens is essential to limit transfer and spread of viral disease and to monitor treatment methods. The need for such methods can be illustrated be the events surrounding the emergence of SARS.

SARS is a viral respiratory illness caused by the SARS-associated coronavirus (SARS-CoV). SARS was first reported in Asia in February 2003. Over the next few months, the illness spread to more than two dozen countries in North America, South America, Europe, and Asia before the SARS global outbreak of 2003 was contained. The symptoms of SARS included high fever, dry cough, and other flu like symptoms that can progress to pneumonia. Death occurred in approximately 15% of the infected patients. The contagious nature of SARS and its fast spread in several countries in Asia caused considerable concern throughout the world.

The SARS coronavirus belongs to a group of viruses similar to those causing the common cold. The SARS virus spreads by close person-to-person contact and is thought to be transmitted most readily by respiratory droplets produced when an infected person coughs or sneezes. Droplet spread can occur when droplets from an infected person are propelled a short distance (generally up to 3 feet) through the air and deposited on the mucus membranes of nearby persons. The virus also can spread when a person touches a surface contaminated with infectious droplets and then touches his or her mouth, nose, or eyes.

In most cases, symptoms of SARS first occur 2 to 5 days after exposure to the virus. However, the incubation period may be up to 2 weeks. Because of the extended incubation period, patients infected with the SARS virus may be placed in quarantine with those who are not infected. This may cause the uninfected patients and medical staff to become exposed to the SARS virus and to develop the symptoms of SARS.

Because of its ease of spread and long incubation period, it is critical to reliably determine the presence of the virus in a patient thought to be infected with SARS. Ideally, such a test should be sufficiently sensitive to detect the virus at an early stage of infection. The test should also be specific and have a low occurrence of false-positive and false-negative results.

Without a reliable test that can be used in the early stages of SARS infection, physicians and health care teams rely on a process of elimination, ruling out other known causes of the severe pneumonia before diagnosing SARS. However, a positive test result for another respiratory pathogen does not completely rule out infection with the SARS virus. Patients can be co-infected with both the SARS virus and other respiratory pathogens.

At present, two types of tests detect the presence of the SARS virus. The first of these is an enzyme immunoassay (EIA) test which detects serum antibody to SARS. The other test is a polymer chain reaction (PCR) test which detects the viral genetic material.

During the course of infection with the SARS virus, levels of specific anti-viral antibodies rise in the blood. Many of the tests currently available for the diagnosis of SARS are based on the detection of such antibodies. Such tests are typically either Enzyme Linked Immunoassays (ELISAs) or immunofluorescence assays (IFAs). With ELISAs, the antibodies cannot be detected until about 20 days after infection. IFAs can detect antibodies approximately 10 days after the initial infection. However, such assays are comparatively slow and require the growth of the virus in a cell culture.

The utility of antibody tests for detecting viruses, such as SARS, may be further limited due to the rapid mutation rate of some viruses. A Canadian study has detected the SARS virus in only 60% of those with SARS infection. Such results suggest that the virus is unstable and is mutating rapidly. This is not unexpected as coronaviruses are notorious for changing their outer surface antigens rapidly, a process termed antigenic drift.

Techniques such as the Polymer Chain Reaction (PCR) allow direct detection of the virus genetic material and, in theory, can detect infection at a very early stage. Many PCR tests use oligonucleotide microchip technology for detecting the virus with throat swabs, sputum or feces. Such tests typically take a few hours to perform and are relatively costly. In addition, currently available PCR methods give 40% of false positive and negative results, making the method ineffective.

Because of the deficiencies of presently available testing methods, there is a need for an improved test enabling the presence of viruses, such as the SARS virus, to be accurately detected at an early stage of infection. Such a test will benefit those showing symptoms of SARS by allowing for the monitoring of the course of their infection and subsequent recovery. In addition, a quick and effective test will benefit persons suspected of having the disease by allowing uninfected persons to be released from quarantine.

There is also the need for an automated test avoiding the need for manual intervention. Such a test will prevent spread of the disease due to infection during the testing process.

SUMMARY

One embodiment of the present invention provides a method for detecting a virus in a sample. The method involves contacting the sample with a peptidal compound capable of being cleaved at a cleavage point by an enzyme to form a first peptidal compound fragment and a second peptidal compound fragment. The enzyme is encoded by a nucleic acid of the virus during replication of the virus and cleaves a polyprotein encoded by the nucleic acid of the virus. A signaling moiety is linked to a portion of the peptidal compound that forms the first peptidal compound fragment. If the virus is present in the sample, the enzyme produced by the virus cleaves the peptidal compound. The virus is detected by observing the signal from the signaling moiety.

In another embodiment, a quenching moiety is linked to a portion of the peptidal compound present in the second peptidal compound fragment. The signaling moiety and the quenching moiety are linked to the peptidal compound at relative positions such that the quenching moiety quenches the signal of the signaling moiety unless the peptidal compound is cleaved at the cleavage point.

In other embodiments, the virus detected is from either the Nidovirus or the Picornavirus virus families. In one embodiment the virus is the SARS virus. In another embodiment the virus is a rhinovirus.

Another aspect of the invention provides a kit for detecting the presence of a virus in a sample. The kit includes a reagent containing a peptidal compound capable of being cleaved at a cleavage point by an enzyme encoded by the viral nucleic acid to form a first peptidal compound fragment and a second peptidal compound fragment. A signaling moiety is linked to a portion of the peptidal compound that forms the first peptidal compound fragment.

Another aspect of the invention provides a composition for detecting a virus in a sample. The composition includes a peptidal compound capable of being cleaved at a cleavage point by an enzyme encoded by the virus to form a first peptidal compound fragment and a second peptidal compound fragment. A signaling moiety is linked to a portion of the peptidal compound that forms the first peptidal compound fragment and a quenching moiety is linked to a portion of the peptidal compound that forms the second peptidal compound fragment. The signaling moiety and the quenching moiety are linked to the peptidal compound at relative positions such that the quenching moiety quenches a signal of the signaling moiety unless the peptidal compound is cleaved at the cleavage point.

BRIEF DESCRIPTION OF THE DRAWINGS

FIG. 2(A) is a Table showing polyprotein cleavage sites for selected species of Picronaviruses. HRV14: Human Rhinovirus 14; HRVb: Human Rhinovirus b; HRV16: Human Rhinovirus 16; Cxa21: Coxsackievirus A21.

FIG. 2(B) is a Table showing polyprotein cleavage sites for selected species of Picornaviruses. HRV14: Human Rhinovirus 14; HRVb: Human Rhinovirus b; HRV16: Human Rhinovirus 16; Cxa21: Coxsackievirus A21.

FIG. 2(C) is a Table showing polyprotein cleavage sites for selected species of Picronaviruses. HRV14: Human Rhinovirus 14; HRVb: Human Rhinovirus b; HRV16: Human Rhinovirus 16; Cxa21: Coxsackievirus A21.

FIG. 2(D) is a Table showing three polyprotein cleavage sites having high hydrolysis rates for selected species of picronaviruses. HRV14: Human Rhinovirus 14; HRVb: I-Human Rhinovirus b; HXV16: Human Rhinovirus 16; Cxa21: Coxsackievirus A21. A consensus peptide is also shown. SEQ ID NOS. of the cleavage sites are as follows:

Figure 1:
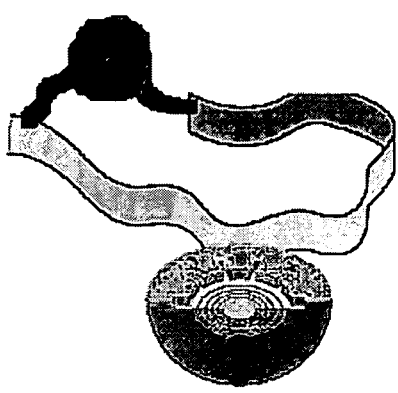
FIG. 1 is a schematic representation of a homogenous assay for the detection of a virus.
Figure 1:
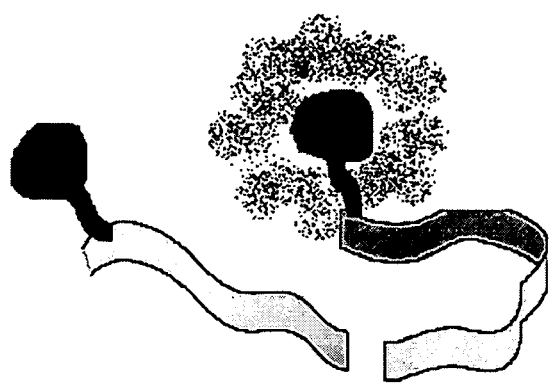

| Cleavage Site | SEQ ID NO |
|---|---|
| HRV 2C 3A | 25 |
| HRVb 2C 3A | 27 |
| Cxa21 2C 3a | 28 |
| HRV16 2C 3A | 26 |
| HRV14 3A 3B | 29 |
| HRVb 3A 3B | 31 |
| Cxa21 3A 3B | 32 |
| HRV16 3A 3B | 30 |
| HRV14 3B 3C | 33 |
| HRVb 3B 3C | 35 |
| Cxa21 3B 3C | 36 |
| HRV16 3B 3C | 34 |

FIG. 3(A) is a Table showing polyprotein cleavage sites for selected species of Nidoviruses. SARS: Human Severe Acute Respiratory Syndrome Virus; BCov: Bovine Coronavirus; HCov: Human Coronavirus.

FIG. 3(B) is a Table showing polyprotein cleavage sites for selected species of Nidoviruses. SARS: Human Severe Acute Respiratory Syndrome Virus; BCov: Bovine Coronavirus; HCov: Human Coronavirus.

FIG. 3(C) is a Table showing polyprotein cleavage sites for selected species of Nidoviruses. SARS: Human Severe Acute Respiratory Syndrome Virus; BCov: Bovine Coronavirus; HCov: Human Coronavirus.

FIG. 3(D) is a Table showing polyprotein cleavage sites for selected species of nidoviruses. SARS: Human Severe Acute Respiratory Syndrome Virus; BCov: Bovine Coronavirus; HCov: Human Coronavirus. SEQ ID NOS. for the 20 residue sequences shown in alignment is as follows:

| Cleavage Site | SEQ ID NO |
|---|---|
| QTSITSAVLQSGFRKM AFPS | 50 |
| VRQCSGVTFQ-GKFKKIVKG | 53 |
| KPCIKVATVQSKMSDVKCTS | 56 |
| EMLDNRATLQAIASEFSSLP | 59 |
| LRANSAVKLQNNELSPVALR | 62 |
| GSLAATVRLQAGNATEVPAN | 65 |
| CDQLREPLMQSADASTFNR | 68 |
| AMYTPHTVLQAVGACVLCNS | 71 |
| IPRRNVATLQAENVTGLFKD | 74 |
| WNTFTR--LQSLENVAYNW | 77 |

DESCRIPTION OF THE EMBODIMENTS

One embodiment of the present invention provides a method of detecting a virus. The method is based on a proteolytic enzyme assay that indicates the presence of the virus by detecting a viral enzyme present during replication of the virus.

Cleavage of the Viral Polyprotein

During the replication of many viruses, such as the SARS virus, human immunodeficiency virus, human papilloma virus, herpes virus, rhinovirus, picomavirus, coronavirus, hepatitis C virus, and others, the viral genetic material is transcribed to form a polyprotein, which is ultimately cleaved into two or more biologically active proteins.

The cleavage of the viral polyprotein into individual proteins is a critical part of the viral life cycle. Many viruses, including those of the adenovirus, baculovirus, comovirus, picomavirus, retrovirus, and togavirus families, encode proteases which cleave the viral polyprotein at these specific cleavage positions to form the active proteins required for viral replication. For example, polyprotein processing during replication of the Cocksfoot mottle virus (genus *Sobemovirus*) is described in Makinen, K. et al., J. Gen. Virol. vol. 81, pp 2783-89 (2000), the contents of which are incorporated by reference.

For the purposes of this invention, a "protease" is an enzyme that catalyses the hydrolysis of a peptide bond. Proteases are part of the hydrolase class of enzymes, which are selected from the enzymatic class having the general reaction equation:

Some virally-encoded proteases cleave only the polyprotein of a specific virus. Others cleave the polyprotein of more than one type of virus. The specificity of protease action arises from the nature of the interaction of the protease at the cleavage region(s) of the polyprotein. A given protease will only cleave the polyprotein at a region having certain defined amino acid sequences. For example, the Rhinovirus HRV14 3C protease will cleave a polyprotein at a Glu-Gly, Glu-Ala or Glu-Gly dipeptide sequence. In addition, the rate of cleavage at these positions varies, depending on the peptide sequence of the polyprotein surrounding the cleavage position.

Thus, a virally-encoded protease can cleave the viral polyprotein at a number of different positions if the amino acid sequence at these positions is such that the cleavage reaction occurs. Similarly, if such sequences are conserved across a number of different viruses, a single protease may cleave the polyprotein of these viruses. The present method takes advantage of this specificity to provide detection methods that are specific for a single virus type or for more than one virus type.

It is believed, but not relied upon for that present invention, that during replication of certain viruses, viral-encoded proteases are autocleaved from the viral polyprotein at an early stage for the viral replication process. For example, the Picornavirus viral polyprotein is processed into the individual protein products by the viral 3C protease. This protease derives from a polypeptide sequence that is itself a part of the viral polyprotein. The mechanism by which this protease becomes cleaved from the viral polyprotein is described in Khan, A. R. et al. "Structural aspects of activation pathways of aspartic protease zymogens and viral 3C protease precursors", Proc. Nat'l . Acad. Sci., Vol. 96, No. 20, pp. 10968-75 (1999), the contents of which are incorporated by reference. For other viruses, the viral protease responsible for cleaving the polyprotein may be encoded separately from the polyprotein.

One embodiment of the present invention provides a method of detecting a virus in a sample obtained from a patient suspected of being infected with the virus. The method is applicable to the detection of the wide range of viruses producing a virally-encoded protease that cleaves the viral polyprotein. For the purposes of this invention, a "virally-encoded protease" or "viral protease" is defined as any protease encoded from the genetic material of a virus and which cleaves a peptide bond in the viral polyprotein during replication of the virus.

Virally-encoded proteases cleave the polyprotein of a wide range of virus families, including the Nidovirus, Herpesvirus, Adenovirus, Retrovirus, Picornavirus and Potyvirus families. Rao, M. B. et al., "Molecular and Biotechnological Aspects of Microbial Proteases", Microbiol. and Mol. Biology Rev., Vol. 62, No. 3, p. 597-635 (1998), the contents of which are incorporated by reference. Table 1 shows some examples of the proteases involved in polyprotein cleavage of viruses associated with various animal and plant diseases. Additional examples of such proteases are described in Corbalenya, A. E. and Snijder, E. J., "Viral cysteine proteinases, Perspectives in Drug Discovery and Design" 6: pp. 64-86 (1996) and Dougherby, W. G. and Semler, B. L., "Expression of virus-encoded protonases: functional and structural similarities with cellular enzymes", Microbiol. Rev. 57, pp. 781-822 (1993), John Ziebuhr et al. "Virus-encoded proteinases and proteolytic processing in the Nidovirales", J. Gen. Vir., Vol. 81, pp. 853-79 (2000), the contents of which are incorporated by reference.

TABLE 1

EXAMPLES OF VIRAL-CODED PROTEASES INVOLVED IN POLYPROTEIN PROCESSING

| Virus | Protease | Associated Disease |
|---|---|---|
| *Picornaviridae* | | |
| Enterovirus | 3C (CSL), 2A(CSL) | Meningitis, gastro-intestinal infections |
| Coxsackievirus | 3C | Common cold |
| Echovirus | 3C | Summer flu, hand-foot-and mouth |
| Poliovirus | 3C | Poliomyelitis |
| Rhinovirus | 3C (CSL), 2A(CSL) | Common cold, asthma exacerbation in allergies |
| Aphthovirus | 3C (CSL), L (Cys) | Foot and mouth disease |
| Cardiovirus | 3C (CSL) | Encephalitis, heart disease (mainly murine, affects other mammals) |
| Hepatovirus | 3C (CSL) | Hepatitis A (chronic jaundice) |
| *Togoviridae* | | |
| Alphaviruses | Cys and Ser | Equine encephalitis |
| Poxyviruses | Ser | Smallpox |
| Rubiviruses | Cys | Rubella (German measles) |
| *Paramyxoviridae* | | |
| Parainfluenza | Ser | Respiratory infection |
| RSV | Ser | Infant bronchiolitis, viral pneumonia |
| *Coronaviridae* | Cys, 3C-like CSL, Ser | Infant bronchiolitis, viral pneumonia |
| SARS | Cys, 3C like, PL1 PL2 | Acute respiratory syndrome |
| Arterivirus | Cys | Pig disease |
| *Flaviviridae* | | |
| Flavivirus | NS3 (Ser, unique), NS2B (Ser, unique) | |
| Yellow-fever virus | NS3 (Ser, unique) | Yellow-fever |
| HepC virus | NS3 (Ser, unique) | Hepatitis C |
| Pestivirus | Cys, Ser | Pigs, cattle and sheep disease |
| *Adenoviridae* | | Acute upper respiratory, eye and intestinal tract, infant death |
| *Herpesviridae* | Herpesviridae | Herpes (systemic and topical) |
| *Retroviridae* | | |
| HIV | Asp | AIDS |
| *Caliciviridae* | 3C-like (CSL) | Rabbit hemorrhagic disease |
| *Potyviridae* | | |
| Potyvirus | NIa (3C-like CSL), HC$^{pro}$ (Cys) | Potato disease |
| Bymovirus | 3C-like (CSL), Cys | Plant disease |
| *Comoviridae* | | |
| Comovirus | p24 (3C-like CSL) | Plant disease |
| Nepovirus | p23 (3C-like CSL) | Plant disease |

Sources
1) Gorbalenya, A. E. and Snijder, E. J., Viral cysteine proteinases, Perspectives in Drug Discovery and Design 6: pp. 64-86 (1996)
2) Dougherby, W. G. and Semler, B. L., Expression of virus-encoded protonases: functional and structural similarities with cellular enzymes, Microbiol. Rev., Vol. 57, pp. 781-822 (1993)

Proteases are subdivided into two major groups, depending on their site of action. Exopeptidases cleave the peptide bond proximal to the amino or carboxy termini of the substrate, whereas endopeptidases cleave peptide bonds distant from the termini of the substrate. Based on the functional group present at the active site, proteases are further classified into four prominent sub-groups. These are serine proteases, aspartic proteases, cysteine proteases, and metalloproteases.

Viruses produce many different proteases, including members of the above classes. For example, the Hepatitis C virus genome encodes a specific serine protease and a metalloprotease (NS2 and NS3) and the Rhinovirus genome encodes cysteine proteases (3C and 2A). The SARS genome encodes a cysteine protease (3CL). Anand K. et al., Coronavirus Main Protease (3CL$^{pro}$) Structure: Basis of Design of Anti-SARS Drugs" Science, Vol. 30, pp. 1763-67 (2003), the contents of which are incorporated by reference. In addition, the SARS genome encodes the PL1 and PL2 main proteases. Each member of the herpesvirus family encodes a unique serine protease. Adenoviruses code for a serine-centered, neutral protease specific for selected Gly-Ala bonds in several virus-encoded precursor proteins. Retroviruses encode an aspartyl protease, which is responsible for processing the gag and pol polyprotein precursors into the structural proteins of the mature virus.

Viral-encoded Enzymes

The cleavage of the polyprotein to produce functional viral proteins is a key step in the virus maturation process. The cleavage step occurs at an early stage of viral replication cycle. This requires that the viral-encoded proteases responsible for this process are themselves present at an early stage of replication. Because the proteases are present early in the cycle of infection, their detection allows viral infection to be confirmed at an early stage.

Tissue infected by a virus contains fully assembled virus particles as well as components of the viral particles. These components include the active proteases. See Sosnovtsev, S. V., et al., "Cleavage of the feline calicivirus capsid precursor is mediated by a virus-encoded proteinase", J. Virol., Vol. 72, pp. 3051-59 (1998), the contents of which are incorporated by reference. It is also known that certain viruses, for example the Influenza types A and B viruses, produce surface glycoproteins with neuraminidase activity whose presence confirms infection with the virus. ZSTATFLU® Product Package Insert (ZymeTx, Inc., Oklahoma City, Okla. 73104)

Detection of Polyprotein Cleaving Proteases

In one embodiment of the present invention, the presence of a viral-encoded protease associated with a virus is detected by observing the cleavage of a peptidal compound having a specific cleavage site for the protease. The specificity of the cleavage reaction depends upon the amino acid sequence at the cleavage site. Specific cleavage sites for many viral-encoded proteases have been identified. See, for example, John Ziebuhr et al. "Virus-encoded proteinases and proteolytic processing in the Nidovirales", J. Gen. Vir., 81, pp. 853-79 (2000), the contents of which is incorporated by reference. The viral cleavage sites are chosen such that their cleavage is specific for the type of virus to be detected. Table 2 shows examples of some viral proteases along with peptides that are specifically cleaved by them.

TABLE 2

EXAMPLES OF SPECIFIC CLEAVAGE PEPTIDES

| Protease | Specific Cleavage Peptides |
|---|---|
| Rhinovirus 3CL | Arg-Pro-Val-Val-Val-Gln-Gly-Pro-Asn SEQ ID NO: 83 |
| Coronavirus TGEV 3CL | Ser-Thr-Leu-Gln-Ser-Gly-Leu-Arg-Lys SEQ ID NO: 84 |

TABLE 2-continued

EXAMPLES OF SPECIFIC CLEAVAGE PEPTIDES

| Protease | Specific Cleavage Peptides |
|---|---|
| SARS COV 3CL | Ala-Thr-Val-Arg-Leu-Gln-Ala-Gly-Phe SEQ ID NO: 85 |
| | Val-Ser-Val-Asn-Ser-Thr-Leu-Gln-Ser-Gly-Leu-Arg-Lys-Met-Ala-Cys SEQ ID NO: 86 |

In the present invention, a region of the viral polyprotein containing a cleavage site for the protease to be detected is mimicked by a peptidal compound. For the purposes of this invention, the term "peptidal compound" is any compound containing a cleavage site for a protease encoded by the virus or viruses that are to be detected. Under appropriate conditions, the protease will cleave the peptidal compound to form a "first peptidal compound fragment" and a "second peptidal compound fragment". The conditions required for performing such enzyme cleavage reactions are well known for those skilled in the art.

A region of the peptidal compound that forms one of the peptidal compound fragments is tagged by directly or indirectly attaching a signaling moiety that allows that fragment to be detected. For the purposes of the invention, the "signaling moiety" can be any label that produces a detectable signal. For example, the signaling moiety can be a detectable label that produces a fluorescencent, a chemiluminescent or a calorimetric signal.

In one embodiment, the cleavage site is specific for a single virus. This allows for a specific test that detects this virus and shows low cross-reactivity for other viruses. In another embodiment, the cleavage site that conserved across more than one virus. This allows for a single test that will detect more than one virus.

It is believed, but not relied upon for the present invention, that since polyprotein-cleaving proteases are not present on the viral surface, they are less subject to mutation than are viral-coat proteins. Also, since these proteases have an important role in the virus life cycle, significant mutation is unlikely.

The method of the present invention can be used to test for the presence of a virus in a sample contaminated with the virus. In one embodiment, the sample is taken from an organism. For example, the method can test for a virus in a sample taken from an animal or plant host. In one embodiment, the method tests for a virus in a sample taken from a human patient. The sample can be mucus, saliva, throat wash, blood, serum, plasma, urine, spinal fluid, sputum, tissue biopsy, broncheoalveolar fluid, vaginal fluid, tear fluid or another biological sample. For example, the SARS virus is known to be present in saliva. Wang, W-K "Detection of SARS-associated Coronavirus in Throat Wash and Saliva in Early Diagnosis" Emerg Infect Dis [serial on the Internet] (June 2004). Available from: http://www.cdc.gov/ncidod/EID/vol10no7/03-1113.htm. The invention includes methods where the sample is treated to disrupt cells to release viral components, including the protease, e.g. by using sonification. The presence of a virus is confirmed by detecting a viral protease produced by the virus. In one embodiment, the protease level is correlated with the level of viral replication or viral load.

In one embodiment of the invention, the peptidal compound includes a sequence of at least four amino acids residues from the sequence in the region of a polyprotein cleavage site, including the protease cleavage site. In another embodiment, the peptidal compound includes at least seven amino acids residues from the protease cleavage site. In another embodiment, the peptidal compound includes at least ten amino acids residues from the protease cleavage site. In yet another embodiment, the peptidal compound includes at least four amino acids from a sequence that is a consensus sequence of the sequences at the cleavage sites of two or more viruses. In other embodiments, the peptidal compound contains at least seven, or at least ten, amino acids from a consensus sequence of the cleavage sites of two or more viruses.

In another embodiment, the one or more amino acids present in the peptidal compound are modified or replaced by an analog. Analogs are amino acids that have a structure similar to the native compound but differ from it in respect to certain components or side chains.

Alternatively, one or more amino acids may be replaced by similar amino acids without altering the cleavage properties of the mimic peptidal compound. Useful conservative substitutions are shown in Table 3, "Preferred substitutions." Conservative substitutions whereby an amino acid of one class is replaced with another amino acid of the same type fall within the scope of the invention so long as the substitution does not materially alter the cleavage properties of the peptidal compound. Such substitutions can be tested using a method such as that described in Example 5 to determine whether the substitution alters the cleavage properties.

TABLE 3

| | Preferred substitutions | |
|---|---|---|
| Original residue | Exemplary substitutions | Preferred substitutions |
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

By selecting a peptidal compound to mimic a particular polyprotein cleavage site, the method of the present invention can be used to test for a wide range of viruses. In one embodiment, the virus detected is from the picornavirus family. This family of viruses includes the human rhinoviruses and the coxsackieviruses. FIGS. 2A-D show the sequences around known cleavage positions in the polyproteins encoded by some such viruses. The viruses shown are Human Rhinovirus 14 (HRV14), Human Rhinovirus b (HRVb), Human Rhinovirus 16 (HRV16) and Coxsackievirus A21 (Cxa21). The figures also show sequence alignment between the cleavage sites of the viruses and consensus peptide sequences. Sequence alignment was performed using the CLUSTAL W (1.82) general purpose sequence analysis program. (European Bioinformatics Institute, available at www.ebi.ac.uk/clustalw).

In the test method for a particular virus, protease cleavage of a peptidal compound containing an amino acid sequence including one of the polypeptide cleavage regions is detected. By selecting a peptidal compound that shows low homology to sequences present in similar viruses, a specific test for the virus can be performed. The invention also includes methods where two or more peptidal compounds are cleaved, either by a single protease or by different proteases.

In another embodiment, the virus detected is a Nidovirus. This class of viruses includes the SARS virus, Bovine Coronavirus and Human Coronavirus. The SARS genome is available at: M. Marra et al., http://www.bcgsc.ca/bioinfo/SARS. The genome shows more than a 44% homology with the coronavirus genome and, like the coronavirus genome, encodes a 3CL protease (Sequence homology performed using the software packages available at EMBL (European Bioinformatics Institute, http://www.ebi.ac.uk/embl/index.html)).

FIGS. 3A-D show the amino acid sequences around known cleavage positions in the polyproteins encoded by these viruses. Sequence alignments between the cleavage sites of the three viruses and consensus sequences are also shown. Sequence alignment was again performed using the CLUSTAL W (1.82) sequence analysis program. FIG. 3(A) shows that the cleavage regions centered at, for example, positions 180 or 818 of the SARS polyprotein shows little homology with the Human or Bovine Coronavirus polyprotein. By choosing peptide sequence mimicking the sequence of one of these cleavage positions, a specific test for the SARS virus can be performed. Similarly, by choosing a Human Coronavirus polyprotein sequence showing low homology to either the SARS or Bovine Coronavirus polyprotein, a specific test for Human Coronavirus can be performed.

Assays for Protease Cleaving Activity

One embodiment of the present invention provides a homogenous assay for the detection of a virus. The chosen peptidal compound is synthesized and linked to a signaling moiety at one side of the cleavage region and to a quencher moiety at the other side of the cleavage region. A "homogeneous assay" is an assay not requiring separation of signaling moiety from other assay components.

For the purposes of the invention, a "quencher moiety" is any substance that is capable of reducing or eliminating the signal emitted by the signaling moiety. For example, the quencher moiety may act by absorption of the signal emitted by the signaling moiety or by an energy transfer mechanism. The distance between the signaling moiety and the quencher moiety is such that presence of the quencher moiety substantially reduces or eliminates the signal emitted from the signaling moiety unless the peptidal compound is cleaved at a position resulting in separation of the signaling and quencher moieties.

In one embodiment, the signaling moiety and quencher moiety are separated by no more than 5 amino acid residues. In another embodiment, the signaling moiety and quencher moiety are separated by no more than 10 amino acid residues. In yet another embodiment, the signaling moiety and quencher moiety are separated by no more than 15 amino acid residues. In yet another embodiment, the signaling moiety and quencher moiety are separated by no more than 20 amino acid residues.

The peptidal compound is contacted with the sample being tested for the presence of a virus. If the virus is present in the sample, the viral protease is also present. This protease cleaves the peptidal compound and a change in the signal from the signaling moiety can be observed. FIG. 1 shows a representation of the cleavage reaction. Such homogenous fluorescent and colorimetric assays are known to those skilled in the art. See, for example: Biochemistry, Allinger, Wang Q. M. et al., "A continuous calorimetric assay for rhinovirus-14 3C protease using peptide p-nitroanilides as substrates" Anal. Biochem. Vol. 252, pp. 238-45 (1997), and Basak S. et al. "In vitro elucidation of substrate specificity and bioassay of proprotein convertase 4 using intramolecularly quenched fluorogenic peptides" Biochem. J. Vol. 380, pp. 505-14 (2004) the contents of which are incorporated by reference. However, it is believed that such methods have not previously been utilized for the diagnosis of viral disease.

In another embodiment of the present invention, the signaling moiety is a chemiluminescent signaling moiety. The chemiluminescent signaling moiety is attached to one side of the cleavage region of the peptidal compound and a fluorescent accepting quencher moiety is attached at the other side of the cleavage region. U.S Pat. No. 6,243,980, the contents of which are incorporated by reference, describes such a detection system, involving the use of a chemiluminescent 1,2-dioxetane compound as the signaling moiety. If the viral protease is not present in the sample, cleavage of the peptidal compound does not occur. The energy from the 1,2-dioxetane decomposition is transferred to the fluorescent accepting moiety and released at a wavelength distinct from the emission spectrum of the 1,2-dioxetane. If the peptidal compound is cleaved, the fluorescent accepting moiety is separated from the 1,2-dioxetane and a chemiluminescent emission from the dioxetane compound is observed.

In another embodiment, the signaling moiety is a fluorescent compound and the quencher moiety is a fluorescent compound having an excitation spectrum that overlaps the emission spectrum of the signaling moiety. Here, the two moieties are separated apart at a distance consistent with fluorescent resonance energy transfer so that the fluorescent moiety is capable of acting as a resonance energy donor.

In another embodiment, a quenching group, such as a non-fluorescent absorbing dye is used in place of the fluorescent accepting quenching moiety. Suitable quenching groups are described in U.S. Pat. No. 6,243,980, the contents of which are incorporated by reference.

In such a test method, the test sample is contacted with the peptidal compound under conditions that allow cleavage of the peptidal compound by the protease if the virus is present in the sample. In one embodiment, the temperature is controlled. For example, the temperature can be controlled at 37 deg C. to provide optimal conditions for the enzyme reaction. The signal from the cleaved peptidal compound fragment is then detected using a detection device appropriate to the label used.

Another embodiment of the present invention provides a heterogeneous assay for the detection of a virus. In one embodiment of the heterogeneous method, a first member of a first binding pair is linked to one side of the cleavage region of the peptidal compound. A first member of a second binding pair, or a signaling moiety, is linked to the other side of the cleavage region of the peptidal compound. A second member of the first binding pair is linked to a solid-phase. Alternatively, one side of the peptide can be linked directly to the solid-phase. A "heterogeneous assay" is an assay in which the solid-phase is separated from another assay component during the assay.

The peptidal compound is incubated with the solid-phase and a sample being tested for the presence of a virus. The incubation conditions are such that binding occurs between the first and second members of the first binding pair. If a protease having the ability to cleave the peptidal compound at the cleavage site is present in the patient sample, the peptidal compound is cleaved causing the peptidal compound fragment linked to the first member of a second binding pair, or the signaling moiety, to become detached from the solid phase.

The solid-phase and liquid phase are then separated. If a signaling moiety is linked to the peptidal compound, the amount of signaling moiety in either the solid phase or the liquid phase is measured to determine the presence of the protease, and hence the virus, in the sample. If a first member of a second binding pair is linked to the peptidal compound, a second member of the second binding pair linked to a signaling moiety is incubated with the peptidal compound under conditions such that binding occurs between the first and second members of the second binding pair. The presence of the virus is then detected as above.

The above steps may be varied or combined without departing from the method of the present invention. For example, those skilled in the art will recognize that, in the heterogeneous assay method, the second member of the second binding pair linked to the signaling moiety can be contacted with the peptidal compound before or at the same time as the solid-phase is contacted with the peptidal compound.

Many different binding pairs may be used for the first and second binding pairs. However, the binding pairs must be chosen such that that the first binding pair does not interact with the second binding pair. Examples of such binding pairs are well known in the art and include biotin/avidin, biotin/strephavidin, antibody/antigen, antibody/hapten, binding protein/bound molecule and complementary nucleic acid sequences. The first member of each binding pair, or the signaling moiety, can be directly linked to the peptide by a covalent bond or indirectly via a spacer molecule having coupling functional groups at each end. Examples of such linkers include an alkyl, a glycol, an ether, a polyether, a polynucleotide and a polypeptide molecule.

Solid-phases suitable for use in the heterogeneous assay include, but are not limited to test tubes, microtiter plates, microtiter wells, beads, dipsticks, polymer microparticles, magnetic microparticles, nitrocellulose, chip arrays and other solid phases familiar to those skilled in the art. The signaling moiety used in the heterogeneous assay may be any label known to those skilled in the art. Such labels include radioactive, calorimetric, fluorescent and luminescent labels.

A heterogeneous chemiluminescent assay for the detection of proteases is described in U.S. Pat. No. 56,243,980, the contents of which are incorporated by reference. Here, the second member of the second binding pair is conjugated with an enzyme, such as alkaline phosphatase, which triggers 1,2-dioxetane to emit a chemiluminescent signal.

In one embodiment, the homogeneous or heterogeneous assay method of the present invention is automated so that a result can be obtained without the need for medical staff to be exposed to a patient thought to be infected by the viral disease under test. For example, the patient can be tested in a clean room (for example, but not limited to P3 type room). The patient can pick up, or get before entering the room, a diagnostic kit, which can include a solid phase coated with a labeled peptide of the type discussed above. For example, the solid phase can be a tissue which was previously immersed with peptide, or a test stick that can be from the type used to test pregnancy. The patient can supply a sample, such as a saliva sample, at a pre-prepared spot on the solid phase.

The solid phase containing the sample is then incubated to allow the enzymatic reaction to occur. In one embodiment, the reaction temperature in controlled at 37° C. to provide optimal conditions for the enzyme reaction. When the incubation is complete, the sample to be tested can be measured on a spectrophotometer, using a remote control, or a mechanical system operated manually from outside the room. The sample can be tested for a qualitative color or UV detection. After the test the sample can be discarded by an automated system, or a remote operated handle that trashes the sample.

Detection of New Emerging Viral Diseases

In another embodiment, the present invention provides a method for developing an assay for the detection of a newly emergent virus. Once the genome of the emergent virus is identified and its reproduction system known, viral proteases and those regions of the viral polyprotein that are cleaved by such proteases can be determined by examining the sequence homology between the sequence of the emergent virus and that of known viruses. Specific mimic peptide compounds bridging the regions cleaved by the protease are then prepared and tested to determine the activity of the polyprotein cleaving protease against each peptide. In one embodiment, the peptide showing the highest rate of cleavage is chosen and used in the preparation of the test for the virus. The cleavage rates of such compounds may be determined using a method such as that described in Orr D.C. et al. "Hydrolysis of a series of synthetic peptide substrates by the human rhinovirus 14 3C proteinase, cloned and expressed in $E.\ coli$", J. Gen. Vir. Vol. 70, pp. 2931-42 (1989), the contents of which are incorporated by reference.

The reason for the effectiveness of the method for new emerging viral diseases is that the basic function of the proteolytic activity is maintained in the overall mechanism of the virus maturation. Specific proteases can be rapidly analyzed once the genome of the new virus has been identified. Thus, a new protease from a new emerging virus is constructed based on the template of a protease from a similar known virus from the same family. For each virus family, a library of peptides can be synthesized and the rate of cleavage by the protease measured. Based on there results, a consensus peptide is chosen, as is shown in Example 5 for rhinovirus.

The proteolytic class of the enzyme can be classified using data in the literature. Several databases exist that include an extensive amount of information about enzymes as they relate to their designated class. For example, Swiss-Prot Enzyme nomenclature database at http://kr.expasy.org/enzyme or classification of enzymes at http://www-biol.paisley.ac.uk/marco/enzyme_electrode/Chapter1/page 1a.htm. The enzyme can be further classified upon sequencing the enzyme and comparing its homology to other enzymes. Often times, the sequence for the enzyme has already been determined and can thus be found in the literature or a database (e.g. Genbank)http://www.ncbi.nlm.nih.gov/Genbank/) or UniProt/Swiss-Prot Protein Knowledgebase (European Bioinformatics Institute at http://www.ebi.ac.uk/swissprot/ or GOR IV Secondary Structure Prediction Method (e.g. http://npsa-pbil.ibcp.fr/cgi-bin/npsa_automat.p1?page=/NPSA/npsa_server.html). If the enzyme sequence has not been identified, the enzyme can be isolated according to a variety of techniques known to those skilled in the art. Additionally, the enzyme can be synthesized using recombinant DNA techniques that are commonly known to scientists practicing in the field of molecular biology (See Short Protocols in Molecular Biology, 2d. ed., John Wiley & Sons (1992), which is incorporated herein by reference.

Sequencing of the target protein can be performed at the amino acid level and/or the DNA level using techniques known to those skilled in such an art. To determine the DNA sequence of the target protein, the method discussed in Wilhelm Arrange, DNA sequencing strategies, Automated and Advanced Approaches, 15 BN 0971136832 (S. Zimmerman, ed.), which is also incorporated herein by reference, can be used. The determined sequence of the enzyme can be compared for homology to other known sequences of classified enzymes having an identified tertiary, or preferably quaternary structure. Information regarding such enzymes are located databases, such as the Brookhaven Crystallographic Data Bank (http://pdb.pdb.bnl.gov).

After categorizing the chemical reactions the enzymes undergo, the specific peptide sequence at the cleavage regions of the viral polyprotein is determined by comparing the genome sequence to a homologous genome. Mimic peptidal compounds are then prepared as described above. In one embodiment, the peptidal compounds contain peptides having 6-15 amino acids from the cleavage regions. A library of such compounds is prepared and the cleavage rate determined for each compound determined. Peptidal compounds having high cleavage rates are then selected for use in viral tests. Kits, Compositions and Reagents for the Detection of Viral Disease The present invention also provides for kits for detecting a viral disease. In one embodiment, the kit contains at least a reagent comprising one the mimic peptidal compounds described above and a buffer in a package or container. In one embodiment, a signaling moiety is linked to a portion of the peptidal compound present in one peptidal compound fragment. In another embodiment, a quencher moiety linked to a portion of the peptidal compound present in the other peptidal compound fragment. The signaling moiety and the quencher moiety are linked to the peptidal compound at relative positions such that the quencher molecule quenches the signal of the reporter molecule unless the peptidal compound is cleaved at the cleavage point.

In another embodiment, the kit contains the following in one or more packages or containers: (a) a construct reagent comprising (i) a peptidal compound capable of being cleaved by the enzyme to form two peptidal compound fragments, (ii) a first member of a first binding pair linked to a portion of the peptidal compound present in one peptide fragment, and (iii) a first member of a second binding pair linked to a portion of the peptidal compound present in the other peptidal compound fragment, (b) a solid-phase reagent comprising a second member of the first binding pair is linked to a solid-phase, and (c) a signaling reagent comprising a second member of the second binding pair linked to a signaling moiety.

In yet another embodiment, the kit contains the following in one or more packages or containers: (a) a construct reagent comprising (i) a peptidal compound capable of being cleaved by the enzyme to form two peptidal compound fragments, (ii) a first member of a first binding pair linked to a portion of the peptidal compound present in one peptidal compound fragment, and (iii) a signaling moiety linked to a portion of the peptidal compound present in the other peptidal compound fragment and (b) a solid-phase reagent comprising a second member of the first binding pair is linked to a solid-phase.

When a kit is supplied, the different components may be packaged in separate containers and admixed immediately before use. Such packaging of the components separately may permit long-term storage without losing the active components' functions. Embodiments in which two or more of components (a)-(c) are found in the same container are also contemplated.

In another embodiment, the above kits further comprise one or more of the following reagents:
(a) a wash buffer reagent for use using heterogeneous assays;
(b) a negative control reagent free of a protease capable of cleaving the construct reagent;
(c) a positive control containing a protease capable of cleaving the construct reagent;
(d) a signal generation reagent for development of a detectable signal from the signaling moiety; and
(d) a sample collection means such as a syringe, throat swab, or other sample collection device.

The reagents included in the kits can be supplied in containers of any sort such that the life of the different components are preserved and are not adsorbed or altered by the materials of the container. For example, sealed glass ampules may contain lyophilized reagents, or buffers that have been packaged under a neutral, non-reacting gas, such as nitrogen. Ampules may consist of any suitable material, such as glass, organic polymers, such as polycarbonate, polystyrene, etc.; ceramic, metal or any other material typically employed to hold similar reagents. Other examples of suitable containers include simple bottles that may be fabricated from similar substances as ampules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc.

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, etc. Detailed instructions may not be physically associated with the kit; instead, a user may be directed to an internet web site specified by the manufacturer or distributor of the kit, or supplied as electronic mail.

In another embodiment, the invention provides a composition for detecting a virus in a sample. The composition includes a buffer and a mimic peptidal compound capable of being cleaved at a cleavage point by a protease produced by the virus to form a first peptidal compound fragment and a second peptidal compound fragment. A signaling moiety is linked to a portion of the peptidal compound present in the first peptidal compound fragment and a quenching moiety is linked to a portion of the peptidal compound present in the second peptidal compound fragment. The signaling moiety and the quenching moiety are linked to the peptidal compound at relative positions such that the quenching moiety quenches a signal of the signaling moiety.

In one embodiment, the virus is a Rhinovirus. In this embodiment, the composition can include a peptidal compound containing an amino acid sequence present one of the cleavage sites on the Rhinovirus polyprotein. For example, the amino acid sequence can be one of the Rhinovirus sequences listed in Table 2.

In another embodiment, the virus is the SARS virus. In this embodiment, can include a peptidal compound can containing an amino acid sequence present one of the cleavage sites on the SARS virus polyprotein. For example, the amino acid sequence can be one of the Rhinovirus sequences listed in Table 3.

A more complete understanding of the present invention can be obtained by reference to the following specific Examples. The Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations. Modifications and variations of the invention as hereinbefore set forth can be made without departing from the spirit and scope thereof, and, therefore, only such limitations should be imposed as are indicated by the appended claims.

EXAMPLES

Example 1

Detection of Protease Activity

Enzymatic activity for 3C protease can be detected using chromogenic substrates as described in: Wang, Q. M. et al. "A continuous colorimetric assay for rhinovirus-14 3C protease using peptide p-nitroanilides as substrates" Anal. Biochem. Vol. 252, pp. 238-45 (1997), the contents of which are incorporated by reference. Tagged substrates are used to determine the ability of the protease to cleave. The first peptide substrate used is tagged using p-nitroaniline. When p-nitroaniline is cleaved from the peptide, a signal is produced. The cleavage causes an aromatic pi-electron system to form, the presence of which absorbs in the 405 nm range of the electromagnetic spectrum. The nanomolar extinction coefficient of the cleaved p-nitroaniline is $10^4$ mole$^{-1}$cm$^{31\ 1}$.

Alternatively, a substrate is constructed having a florescent tag attached to one end and a quencher attached to the other end. When the peptide is cleaved fluorescence is detected. Other tags use a similar principle using color reactions.

Example 2

Homogenous Fluorescence Resonance Energy Transfer Assay for 3C Protease

Human Rhinovirus serotype 1A (ATCC) is used to clone the 3C Protease into the expression vector pET16-b and transformed for production into the *E. coli* strain BL21-DE3-pLys-S. 3C Protease expression is induced with 1 mM IPTG at 25° C. and purified from the soluble protein extract by chromatography on a SourceQ (Pharmacia) followed by gel filtration. HRV 3CP activity was measured by fluorescence resonance energy transfer using a dimodified decapeptide substrate MOC-Arg-Ala-Glu-Leu-Gln-Gly-Pro-Tyr-Asp-Lys-DNP-NH2 (SEQ ID NO: 113) (7-methoxy coumarin-4-acetic acid fluorochrome and dinitrophenol quencher) with a Km value of 16.8 μM. Inhibition was measured as a change in initial velocity (V0) as a function of inhibitor (I) concentration and substrate (S) concentration.

Assays are performed in 100 uL volumes in a 96 well format at 30° C. containing 25 mM Tris HCl pH 8.0, 150 mM NaCl, 1 mM EDTA pH 8.0, 6 mM DTT, 2-6 uM substrate, 2% DMSO, 416 nM 3CP and inhibitor as needed. Fluorescence is monitored by excitation at 328 nm and emission at 393 nm with 10 nm cutoffs. Data are analyzed with the nonlinear regression analysis program EnzFitter (BioSoft) with the equation:

$$K_i = (I/((V_{max} \times S)/V_0)/K_s) - I - S$$

Substrate concentrations used are lower than the $K_m$ of the substrate (16.8 uM) so no corrections for an $S/K_m$ term were used.

Example 3

Using the CELLSCAN® Cytometer to Detect Protease Activity

The CELLSCAN® (Medis Technologies Ltd., New York, N.Y.) is a cytometer that can monitor the fluorescence intensity and polarization by using fluorescence probes within individual, non-adherent living cells and can also be used to detect protease activity. The heart of the CELLSCAN is a Cell carrier that contains up to 10,000 wells. A description of the CELLSCAN cytometer and its other uses for diagnosis of cancer and autoimmune diseases is available at: www.medis-el.com.

A CELLSCAN probe is loaded with a specific peptidal compound. For example, the peptidal compound can contain a peptide that is specific for SARS. The peptidal compound is tagged with a fluorescent group on one side of the cleavage region and a quencher on the other. The sample under test, e.g. saliva or mucus, is loaded on the probe If active protease exists, the CELLSCAN will detect fluorescence caused by the cleaved peptide. The presence of active protease and its concentration in the saliva is an indication of an active virus and serves as an indication for the contagious status of the patient.

Example 4

Paper-tissue-Based Automated System for the Detection of SARS

A solution of a color-tagged peptidal compound specific for 3Cl-SARS protease is prepared. The peptide is prepared in a pH 7.0 buffer solution in a millimolar concentration. A tissue (wet-wipes tissues) is immersed in the peptidal compound solution and is kept moist. The saliva or mucus specimen suspected of containing the SARS virus is put in contact with the tissue. If the SARS virus is present, the 3CL SARS protease cleaves the tagged peptide sequence and a color reaction occurs.

Several possibilities exist for detection of the colored reaction product. For a qualitative analysis, a color reaction may be detected visually. For a qualitative analysis, the tissue is transferred to spectrophotometric analyzer for either fluorescence or color detection. The process can be automated so as to protect those performing the assay from infection.

Example 5

Determining an Optimal Peptide Sequence for a Rhinovirus Assay

The cleavage sites of the Rhinovirus HRV14 3C protease are aligned as shown in Table 4. Table 4 also shows the QG dipeptides that appear in the HRV14 primary sequence, showing the six sites that are cleaved. The QA and EG dipeptide sites are also shown. One of each of these sites is known to be cleaved.

TABLE 4

QG DIPEPTIDES THAT APPEAR IN THE HRV14 PRIMARY SEQUENCE

| Location on polyprotein | Sequence | Cleavage Site |
|---|---|---|
| QG Site | | |
| 331 | SEQ ID NO: 87 KSIVPQGLPTTT | IB1C |
| 1,002 | SEQ ID NO: 88 CIAEEQGLSDYI | 2A2B |
| 1,429 | SEQ ID NO: 89 LETLFQGPVYKD | 2C3A |
| 1,514 | SEQ ID NO: 90 LFAQTQGPYSGN | 3A3B |
| 1,537 | SEQ ID NO: 91 RPVVVQGPNTEF | 3B3C |
| 1,704 | SEQ ID NO: 92 GGNGRQGFSAQL | |
| 1,719 | SEQ ID NO: 93 YFVEKQGQVIAR | 3C3D |
| QA Site | | |
| 716 | SEQ ID NO: 94 SNLVVQAMYVPH | |
| 950 | SEQ ID NO: 95 YPSRFQAGVMKG | |
| 1,099 | SEQ ID NO: 96 PYIERQANDGWF | 2B2C |
| 1,139 | SEQ ID NO: 97 NKVLPQAKEKLE | |
| 1,485 | SEQ ID NO: 98 ERAMNQASMIIN | |
| EG Site | | |
| 205 | SEQ ID NO: 99 QLASH EGGNVSV | |
| 567 | SEQ ID NO: 100 TVALTEGLGDEL | IC1D |
| 940 | SEQ ID NO: 101 TNIWIEGSPYYP | |
| 982 | SEQ ID NO: 102 GLLTAEGSGYVC | |
| 1,632 | SEQ ID NO: 103 ISEDLEGVDATL | |
| 2,001 | SEQ ID NO: 104 EIYVVEGGMPSG | |

The cleavage peptides that mimic the cleavage sites for rhinovirus HRV14 are constructed and presented in Table 5.

TABLE 5

CLEAVAGE PEPTIDES

| Cleavage Peptide | Cleavage site Mimicked | Peptide |
|---|---|---|
| SEQ ID NO: 105 DSLETLFQGPVYK | 2C/3A | I |
| SEQ ID NO: 106 EAIAEEQGLSDYIT | 2A/2B | II |
| SEQ ID NO: 107 VPYIERQANDGWFRK | 2B/2C | III |
| SEQ ID NO: 108 RSKSIVPQGLPTTTY | 1B/1C | IV |
| SEQ ID NO: 109 SQTVALTEGLGDELEEY | 1C/1D | V |
| SEQ ID NO: 110 KLFAQTQGPYSGNP | 3A/3B | VI |
| SEQ ID NO: 111 YRPVVVQGPNTEF | 3B/3C | VII |
| SEQ ID NO: 112 KQYFVEKQGQVIAR | 3C/3D | VIII |

Next, the rate of hydrolysis for each of the peptidal compounds is determined. The assay used is a fluorometric, or HPLC based or UV based assay. Such assays are well

TABLE 7-continued

ALINGMENT OF CLEAVAGE SITES FOR DIFFERENT CORNA VIRUSES AND COXACIVIRUSES

| | | | | | | | | | | | | | | | | | | | |
|---|---|---|---|---|---|---|---|---|---|---|---|---|---|---|---|---|---|---|---|
| HUMAN COXACIVIRUS COXB4 SED ID NO: 125 | v | g | a | t | l | e | a | l | F | Q | G | p | p | v | y | r | e | i | k | i |
| SWINE VESICULAR DISEASE VIRUS SVDVH SED ID NO: 126 | v | g | a | t | l | e | a | l | F | Q | G | p | p | v | y | r | e | i | k | i |
| SWINE VESICULAR DISEASE VIRUS SVDVU SED ID NO: 127 | v | g | a | t | l | e | a | l | F | Q | G | p | p | v | y | r | e | i | k | i |
| HUMAN COXACIVIRUS COXB3 SED ID NO: 128 | v | g | t | t | l | e | a | l | F | Q | G | p | p | v | y | r | e | i | k | i |
| HUMAN ENTEROVIRUS HUEV7 SED ID NO: 129 | t | q | d | k | l | e | a | l | F | Q | G | p | p | t | f | k | e | i | k | i |
| HUMAN RHINOVIRUS HRV1B SED ID NO: 130 | v | v | d | v | m | s | a | i | F | Q | G | p | i | s | l | d | a | p | p | p |
| HUMAN RHINOVIRUS HRV2 SED ID NO: 131 | v | v | d | v | m | t | a | i | F | Q | G | p | i | d | m | k | n | p | p | p |
| HUMAN RHINOVIRUS HRV89 SED ID NO: 132 | a | a | q | a | m | e | a | i | F | Q | G | i | d | l | q | s | p | p | p | p |
| HUMAN RHINOVIRUS HRV14 SED ID NO: 133 | i | t | d | s | l | e | t | l | F | Q | G | p | v | y | k | d | l | e | i | d |

---

I claim:

1. A method for determining the presence of a Nidovirus or Picornavirus virus in a sample suspected of containing said virus, the method comprising:
    Contacting a sample with a substrate peptide comprising at least four amino acid residues and capable of being cleaved at a cleavage point by an enzyme to form a cleaved first peptide fragment and a second peptide fragment; and
    detecting the virus by observing the signal from a signaling moiety linked to the substrate peptide;
    wherein the enzyme is encoded by nucleic acid of the virus and is present in the sample;
    wherein said substrate peptide comprises an amino acid sequence identical to a sequence of a polyprotein cleavage region of said enzyme and including said cleavage point;
    wherein said peptide cleavage fragments are peptide fragments of the substrate peptide;
    wherein a signaling moiety is linked to a portion of the peptide present in the first peptide fragment; and
    wherein said method is a heterogeneous assay method.

2. The method of claim 1, wherein a quenching moiety is linked to a portion of the peptide present in the second peptide fragment and wherein the signaling moiety and the quenching moiety are linked to the peptide at relative positions such that the quenching moiety quenches the a signal of the signaling moiety unless the peptide is cleaved at the cleavage point.

3. The method of claim 1, further comprising contacting the sample with a second peptide comprising at least four amino acid residues and capable of being cleaved at a cleavage point by a second enzyme, wherein the second enzyme is encoded by the viral nucleic acid, and wherein said second peptide comprises an amino acid sequence identical to a sequence of a polyprotein cleavage region of said second enzyme and including said cleavage point.

4. The method of claim 1, wherein the enzyme is a protease.

5. The method of claim 1, wherein the signal of the signaling moiety is selected from a group consisting of a moiety emitting a fluorescent signal, a colorimetric signal, and a chemiluminescent signal.

6. The method of claim 5, wherein the signal of the signaling moiety emits a fluorescent signal.

7. The method of claim 1, wherein the virus is detected in a sample taken from an animal thought to be infected by the virus.

8. The method of claim 7, wherein the animal is human.

9. The method of claim 8, wherein the sample is selected from a group consisting of mucus, saliva, blood, serum, plasma, urine, spinal fluid, sputum, tissue biopsy, broncheoalveolar fluid, and tears.

10. The method of claim 1, wherein the virus is a Rhinovirus.

11. The method of claim 1, wherein said peptide comprises at least seven amino acid residues.

12. The method of claim 1, wherein said peptide comprises at least ten amino acid residues.

* * * * *

```
                         SEQUENCE LISTING

<160> NUMBER OF SEQ ID NOS: 133

<210> SEQ ID NO 1
<211> LENGTH: 20
<212> TYPE: PRT
<213> ORGANISM: Human rhinovirus 14

<400> SEQUENCE: 1

Leu Met Leu Lys Gly Ala Pro Ala Leu Asn Ser Pro Asn Val Glu Ala
1               5                  10                  15

Cys Gly Tyr Ser
            20

<210> SEQ ID NO 2
<211> LENGTH: 20
<212> TYPE: PRT
<213> ORGANISM: Human rhinovirus 16

<400> SEQUENCE: 2

Val Leu Glu Lys Gly Ile Pro Thr Leu Gln Ser Pro Ser Val Glu Ala
1               5                  10                  15

Cys Gly Tyr Ser
            20
```

```
<210> SEQ ID NO 3
<211> LENGTH: 20
<212> TYPE: PRT
<213> ORGANISM: Human Rhinovirus b

<400> SEQUENCE: 3

Leu Met Leu Lys Gly Ala Pro Ala Leu Asn Ser Pro Asn Val Glu Ala
1               5                   10                  15

Cys Gly Tyr Ser
            20

<210> SEQ ID NO 4
<211> LENGTH: 20
<212> TYPE: PRT
<213> ORGANISM: Coxsackievirus A21

<400> SEQUENCE: 4

Leu Met Leu Lys Thr Ala Pro Ala Leu Asn Ser Pro Asn Val Glu Ala
1               5                   10                  15

Cys Gly Tyr Ser
            20

<210> SEQ ID NO 5
<211> LENGTH: 20
<212> TYPE: PRT
<213> ORGANISM: Human rhinovirus 14

<400> SEQUENCE: 5

Gly Ile Arg Ser Lys Ser Ile Val Pro Gln Gly Leu Pro Thr Thr Thr
1               5                   10                  15

Leu Pro Gly Ser
            20

<210> SEQ ID NO 6
<211> LENGTH: 20
<212> TYPE: PRT
<213> ORGANISM: Human rhinovirus 16

<400> SEQUENCE: 6

Ser Gly Ala Arg Ala Lys Thr Val Val Gln Gly Leu Pro Val Tyr Val
1               5                   10                  15

Thr Pro Gly Ser
            20

<210> SEQ ID NO 7
<211> LENGTH: 20
<212> TYPE: PRT
<213> ORGANISM: Human Rhinovirus b

<400> SEQUENCE: 7

Gly Ile Arg Ser Lys Ser Ile Val Pro Gln Gly Leu Pro Thr Thr Thr
1               5                   10                  15

Leu Pro Gly Ser
            20

<210> SEQ ID NO 8
<211> LENGTH: 20
<212> TYPE: PRT
<213> ORGANISM: Coxsackievirus A21

<400> SEQUENCE: 8

Leu Arg Asn Ile Thr Val Pro Val His Gln Gly Leu Pro Thr Met Asn
```

```
                1               5                   10                  15

Thr Pro Gly Ser
            20

<210> SEQ ID NO 9
<211> LENGTH: 20
<212> TYPE: PRT
<213> ORGANISM: Human rhinovirus 14

<400> SEQUENCE: 9

Phe Lys Leu Arg Leu Met Lys Asp Thr Gln Thr Ile Ser Gln Thr Val
1               5                   10                  15

Ala Leu Thr Glu
            20

<210> SEQ ID NO 10
<211> LENGTH: 20
<212> TYPE: PRT
<213> ORGANISM: Human rhinovirus 16

<400> SEQUENCE: 10

Leu His Lys Gln Thr Gly Pro Ile Thr Gln Asn Pro Val Glu Arg Tyr
1               5                   10                  15

Val Asp Glu Val
            20

<210> SEQ ID NO 11
<211> LENGTH: 20
<212> TYPE: PRT
<213> ORGANISM: Human Rhinovirus b

<400> SEQUENCE: 11

Thr Ile Ser Gln Thr Val Ala Leu Thr Glu Gly Leu Gly Asp Glu Leu
1               5                   10                  15

Glu Glu Val Ile
            20

<210> SEQ ID NO 12
<211> LENGTH: 20
<212> TYPE: PRT
<213> ORGANISM: Coxsackievirus A21

<400> SEQUENCE: 12

Ser Gln Ser Lys Leu Ile Gly Arg Thr Gln Gly Ile Glu Asp Leu Ile
1               5                   10                  15

Asp Thr Ala Ile
            20

<210> SEQ ID NO 13
<211> LENGTH: 20
<212> TYPE: PRT
<213> ORGANISM: Human rhinovirus 14

<400> SEQUENCE: 13

Lys Lys Arg Lys Gly Asp Ile Lys Ser Tyr Gly Leu Gly Pro Arg Tyr
1               5                   10                  15

Gly Gly Ile Tyr
            20

<210> SEQ ID NO 14
<211> LENGTH: 20
<212> TYPE: PRT
```

<213> ORGANISM: Human rhinovirus 16

<400> SEQUENCE: 14

Ile Arg Pro Arg Thr Asn Leu Thr Thr Val Gly Pro Ser Asp Met Tyr
1               5                   10                  15

Val His Val Gly
            20

<210> SEQ ID NO 15
<211> LENGTH: 20
<212> TYPE: PRT
<213> ORGANISM: Human Rhinovirus b

<400> SEQUENCE: 15

Lys Lys Arg Lys Gly Asp Ile Lys Ser Tyr Gly Leu Gly Pro Arg Tyr
1               5                   10                  15

Gly Gly Ile Tyr
            20

<210> SEQ ID NO 16
<211> LENGTH: 20
<212> TYPE: PRT
<213> ORGANISM: Coxsackievirus A21

<400> SEQUENCE: 16

Leu Thr Lys Val Asp Ser Ile Thr Thr Phe Gly Phe Gly His Gln Asn
1               5                   10                  15

Lys Ala Val Tyr
            20

<210> SEQ ID NO 17
<211> LENGTH: 20
<212> TYPE: PRT
<213> ORGANISM: Human rhinovirus 14

<400> SEQUENCE: 17

Arg Gln Leu Glu Cys Ile Ala Glu Glu Gln Gly Leu Ser Asp Tyr Ile
1               5                   10                  15

Thr Gly Leu Gly
            20

<210> SEQ ID NO 18
<211> LENGTH: 20
<212> TYPE: PRT
<213> ORGANISM: Human rhinovirus 16

<400> SEQUENCE: 18

Leu Arg His Phe His Cys Ala Glu Glu Gln Gly Ile Thr Asp Tyr Ile
1               5                   10                  15

His Met Leu Gly
            20

<210> SEQ ID NO 19
<211> LENGTH: 20
<212> TYPE: PRT
<213> ORGANISM: Human Rhinovirus b

<400> SEQUENCE: 19

Arg Gln Leu Glu Cys Ile Ala Glu Glu Gln Gly Leu Ser Asp Tyr Ile
1               5                   10                  15

Thr Gly Leu Gly
            20

<210> SEQ ID NO 20
<211> LENGTH: 20
<212> TYPE: PRT
<213> ORGANISM: Coxsackievirus A21

<400> SEQUENCE: 20

Trp Val Tyr Glu Glu Glu Ala Met Glu Gln Gly Ile Thr Ser Tyr Ile
1 5 10 15

Glu Ser Leu Gly
20

<210> SEQ ID NO 21
<211> LENGTH: 20
<212> TYPE: PRT
<213> ORGANISM: Human rhinovirus 14

<400> SEQUENCE: 21

His Phe Gln Val Pro Tyr Ile Glu Arg Gln Ala Asn Asp Gly Trp Phe
1 5 10 15

Arg Lys Phe Asn
20

<210> SEQ ID NO 22
<211> LENGTH: 20
<212> TYPE: PRT
<213> ORGANISM: Human rhinovirus 16

<400> SEQUENCE: 22

Trp Thr Gln Leu Thr Tyr Ile His Lys Glu Ser Asp Ser Trp Leu Lys
1 5 10 15

Lys Phe Thr Glu
20

<210> SEQ ID NO 23
<211> LENGTH: 20
<212> TYPE: PRT
<213> ORGANISM: Human Rhinovirus b

<400> SEQUENCE: 23

His Phe Gln Val Pro Tyr Ile Glu Arg Gln Ala Asn Asp Gly Trp Phe
1 5 10 15

Arg Lys Phe Asn
20

<210> SEQ ID NO 24
<211> LENGTH: 20
<212> TYPE: PRT
<213> ORGANISM: Coxsackievirus A21

<400> SEQUENCE: 24

Leu Leu Glu Ile Pro Tyr Val Met Arg Gln Gly Asp Gly Trp Met Lys
1 5 10 15

Lys Phe Thr Glu
20

<210> SEQ ID NO 25
<211> LENGTH: 20
<212> TYPE: PRT
<213> ORGANISM: Human rhinovirus 14

<400> SEQUENCE: 25

-continued

Ile Thr Asp Ser Leu Glu Thr Leu Phe Gln Gly Pro Val Tyr Lys Asp
1               5                   10                  15

Leu Glu Ile Asp
            20

<210> SEQ ID NO 26
<211> LENGTH: 20
<212> TYPE: PRT
<213> ORGANISM: Human rhinovirus 16

<400> SEQUENCE: 26

Val Val Asp Val Met Ser Ala Ile Phe Gln Gly Pro Ile Ser Met Asp
1               5                   10                  15

Lys Pro Pro Pro
            20

<210> SEQ ID NO 27
<211> LENGTH: 20
<212> TYPE: PRT
<213> ORGANISM: Human Rhinovirus b

<400> SEQUENCE: 27

Ile Thr Asp Ser Leu Glu Thr Leu Phe Gln Gly Pro Val Tyr Lys Asp
1               5                   10                  15

Leu Glu Ile Asp
            20

<210> SEQ ID NO 28
<211> LENGTH: 20
<212> TYPE: PRT
<213> ORGANISM: Coxsackievirus A21

<400> SEQUENCE: 28

Ile Gly Asn Cys Met Glu Ala Leu Phe Gln Gly Pro Leu Arg Tyr Lys
1               5                   10                  15

Asp Leu Lys Ile
            20

<210> SEQ ID NO 29
<211> LENGTH: 20
<212> TYPE: PRT
<213> ORGANISM: Human rhinovirus 14

<400> SEQUENCE: 29

Val Ile Tyr Lys Leu Phe Ala Gln Thr Gln Gly Pro Tyr Ser Gly Asn
1               5                   10                  15

Pro Pro His Asn
            20

<210> SEQ ID NO 30
<211> LENGTH: 20
<212> TYPE: PRT
<213> ORGANISM: Human rhinovirus 16

<400> SEQUENCE: 30

Ile Ile Tyr Lys Leu Phe Cys Ser Leu Gln Gly Pro Tyr Ser Gly Glu
1               5                   10                  15

Pro Lys Pro Lys
            20

<210> SEQ ID NO 31
<211> LENGTH: 20

```
<212> TYPE: PRT
<213> ORGANISM: Human Rhinovirus b

<400> SEQUENCE: 31

Val Ile Tyr Lys Leu Phe Ala Gln Thr Gln Gly Pro Tyr Ser Gly Asn
1               5                   10                  15

Pro Pro His Asn
            20

<210> SEQ ID NO 32
<211> LENGTH: 20
<212> TYPE: PRT
<213> ORGANISM: Coxsackievirus A21

<400> SEQUENCE: 32

Val Met Tyr Lys Leu Phe Ala Gly Gln Gln Gly Ala Tyr Thr Gly Leu
1               5                   10                  15

Pro Asn Lys Lys
            20

<210> SEQ ID NO 33
<211> LENGTH: 20
<212> TYPE: PRT
<213> ORGANISM: Human rhinovirus 14

<400> SEQUENCE: 33

Ala Pro Thr Leu Arg Pro Val Val Val Gln Gly Pro Asn Thr Glu Phe
1               5                   10                  15

Ala Leu Ser Leu
            20

<210> SEQ ID NO 34
<211> LENGTH: 20
<212> TYPE: PRT
<213> ORGANISM: Human rhinovirus 16

<400> SEQUENCE: 34

Lys Val Pro Glu Arg Arg Val Val Ala Gln Gly Pro Glu Glu Glu Phe
1               5                   10                  15

Gly Met Ser Ile
            20

<210> SEQ ID NO 35
<211> LENGTH: 20
<212> TYPE: PRT
<213> ORGANISM: Human Rhinovirus b

<400> SEQUENCE: 35

Ala Pro Thr Leu Arg Pro Val Val Val Gln Gly Pro Asn Thr Glu Phe
1               5                   10                  15

Ala Leu Ser Leu
            20

<210> SEQ ID NO 36
<211> LENGTH: 20
<212> TYPE: PRT
<213> ORGANISM: Coxsackievirus A21

<400> SEQUENCE: 36

Val Pro Thr Ile Arg Val Ala Lys Val Gln Gly Pro Gly Phe Asp Tyr
1               5                   10                  15

Ala Val Ala Met
```

-continued

```
<210> SEQ ID NO 37
<211> LENGTH: 20
<212> TYPE: PRT
<213> ORGANISM: Human rhinovirus 14

<400> SEQUENCE: 37

Leu Lys Lys Gln Tyr Phe Val Glu Lys Gln Gly Gln Val Ile Ala Arg
1               5                   10                  15

His Lys Val Arg
            20

<210> SEQ ID NO 38
<211> LENGTH: 20
<212> TYPE: PRT
<213> ORGANISM: Human rhinovirus 16

<400> SEQUENCE: 38

Leu Leu Arg Ser Tyr Phe Thr Glu Gln Gln Gly Gln Ile Gln Ile Ser
1               5                   10                  15

Lys His Val Lys
            20

<210> SEQ ID NO 39
<211> LENGTH: 20
<212> TYPE: PRT
<213> ORGANISM: Human Rhinovirus b

<400> SEQUENCE: 39

Leu Lys Lys Gln Tyr Phe Val Glu Lys Gln Gly Gln Val Ile Ala Arg
1               5                   10                  15

His Lys Val Arg
            20

<210> SEQ ID NO 40
<211> LENGTH: 20
<212> TYPE: PRT
<213> ORGANISM: Coxsackievirus A21

<400> SEQUENCE: 40

Leu Lys Arg Ser Tyr Phe Thr Gln Asn Gln Gly Glu Ile Gln Trp Met
1               5                   10                  15

Arg Ser Ser Lys
            20

<210> SEQ ID NO 41
<211> LENGTH: 20
<212> TYPE: PRT
<213> ORGANISM: SARS: Human Severe Acute Respiratory Syndrome Virus

<400> SEQUENCE: 41

Arg Glu Leu Thr Arg Glu Leu Asn Gly Gly Ala Val Thr Arg Tyr Val
1               5                   10                  15

Asp Asn Asn Phe
            20

<210> SEQ ID NO 42
<211> LENGTH: 20
<212> TYPE: PRT
<213> ORGANISM: Bovine coronavirus

<400> SEQUENCE: 42
```

```
Met Ser Lys Ile Asn Lys Tyr Gly Leu Glu Val Lys Pro Leu Leu Tyr
1               5                   10                  15

Val Asp Gln Tyr
            20

<210> SEQ ID NO 43
<211> LENGTH: 20
<212> TYPE: PRT
<213> ORGANISM: Human coronavirus

<400> SEQUENCE: 43

Asp Val Val Phe Gly Lys Arg Gly Gly Gly Asn Val Thr Tyr Thr Asp
1               5                   10                  15

Gln Tyr Leu Cys
            20

<210> SEQ ID NO 44
<211> LENGTH: 20
<212> TYPE: PRT
<213> ORGANISM: SARS: Human Severe Acute Respiratory Syndrome Virus

<400> SEQUENCE: 44

Thr Asn Asn Val Phe Arg Leu Lys Gly Gly Ala Pro Ile Lys Gly Val
1               5                   10                  15

Thr Phe Gly Glu
            20

<210> SEQ ID NO 45
<211> LENGTH: 20
<212> TYPE: PRT
<213> ORGANISM: Bovine coronavirus

<400> SEQUENCE: 45

Leu Asp Gln Ala Trp Arg Val Pro Cys Ala Gly Arg Arg Val Thr Phe
1               5                   10                  15

Lys Glu Gln Pro
            20

<210> SEQ ID NO 46
<211> LENGTH: 20
<212> TYPE: PRT
<213> ORGANISM: Human coronavirus

<400> SEQUENCE: 46

Leu Pro Val Ala Phe Thr Lys Ala Ala Gly Gly Lys Val Ser Phe Ser
1               5                   10                  15

Asp Asp Val Glu
            20

<210> SEQ ID NO 47
<211> LENGTH: 20
<212> TYPE: PRT
<213> ORGANISM: SARS: Human Severe Acute Respiratory Syndrome Virus

<400> SEQUENCE: 47

Ile Thr Thr Lys Ile Ser Leu Lys Gly Gly Lys Ile Val Ser Thr Cys
1               5                   10                  15

Phe Lys Leu Met
            20

<210> SEQ ID NO 48
```

```
<211> LENGTH: 20
<212> TYPE: PRT
<213> ORGANISM: Bovine coronavirus

<400> SEQUENCE: 48

Leu Thr Thr Pro Phe Ser Leu Lys Gly Gly Ala Val Phe Ser Tyr Phe
1               5                   10                  15

Val Tyr Val Cys
            20

<210> SEQ ID NO 49
<211> LENGTH: 20
<212> TYPE: PRT
<213> ORGANISM: Human coronavirus

<400> SEQUENCE: 49

Ala Thr Ser Ile Val Ala Lys Gln Gly Ala Gly Asp Ala Gly His Ser
1               5                   10                  15

Leu Thr Trp Leu
            20

<210> SEQ ID NO 50
<211> LENGTH: 20
<212> TYPE: PRT
<213> ORGANISM: SARS: Human Severe Acute Respiratory Syndrome Virus

<400> SEQUENCE: 50

Gln Thr Ser Ile Thr Ser Ala Val Leu Gln Ser Gly Phe Arg Lys Met
1               5                   10                  15

Ala Phe Pro Ser
            20

<210> SEQ ID NO 51
<211> LENGTH: 20
<212> TYPE: PRT
<213> ORGANISM: Bovine coronavirus

<400> SEQUENCE: 51

Thr Ala Ser Val Ser Thr Ser Phe Leu Gln Ser Gly Ile Val Lys Met
1               5                   10                  15

Val Asn Pro Thr
            20

<210> SEQ ID NO 52
<211> LENGTH: 20
<212> TYPE: PRT
<213> ORGANISM: Human coronavirus

<400> SEQUENCE: 52

Pro Thr Val Ser Tyr Gly Ser Thr Leu Gln Ala Gly Leu Arg Lys Met
1               5                   10                  15

Ala Gln Pro Ser
            20

<210> SEQ ID NO 53
<211> LENGTH: 20
<212> TYPE: PRT
<213> ORGANISM: SARS: Human Severe Acute Respiratory Syndrome Virus

<400> SEQUENCE: 53

Val Arg Gln Cys Ser Gly Val Thr Phe Gln Gly Lys Phe Lys Lys Ile
1               5                   10                  15
```

-continued

```
Val Lys Gly Thr
            20

<210> SEQ ID NO 54
<211> LENGTH: 20
<212> TYPE: PRT
<213> ORGANISM: Bovine coronavirus

<400> SEQUENCE: 54

Tyr Gln Gln Leu Ala Gly Ile Lys Leu Gln Ser Lys Arg Thr Arg Leu
1               5                   10                  15

Val Lys Gly Ile
            20

<210> SEQ ID NO 55
<211> LENGTH: 20
<212> TYPE: PRT
<213> ORGANISM: Human coronavirus

<400> SEQUENCE: 55

Val Lys Gln Met Phe Gly Val Asn Leu Gln Ser Gly Lys Thr Thr Ser
1               5                   10                  15

Met Phe Lys Ser
            20

<210> SEQ ID NO 56
<211> LENGTH: 20
<212> TYPE: PRT
<213> ORGANISM: SARS: Human Severe Acute Respiratory Syndrome Virus

<400> SEQUENCE: 56

Lys Pro Cys Ile Lys Val Ala Thr Val Gln Ser Lys Met Ser Asp Val
1               5                   10                  15

Lys Cys Thr Ser
            20

<210> SEQ ID NO 57
<211> LENGTH: 20
<212> TYPE: PRT
<213> ORGANISM: Bovine coronavirus

<400> SEQUENCE: 57

Val Pro Ile Ile Glu Val Ser Gln Phe Gln Ser Lys Leu Thr Asp Val
1               5                   10                  15

Lys Cys Ala Asn
            20

<210> SEQ ID NO 58
<211> LENGTH: 20
<212> TYPE: PRT
<213> ORGANISM: Human coronavirus

<400> SEQUENCE: 58

Pro Arg Thr Ile Lys Val Ser Thr Val Gln Ser Lys Leu Thr Asp Leu
1               5                   10                  15

Lys Cys Thr Asn
            20

<210> SEQ ID NO 59
<211> LENGTH: 20
<212> TYPE: PRT
<213> ORGANISM: SARS: Human Severe Acute Respiratory Syndrome Virus
```

-continued

```
<400> SEQUENCE: 59

Glu Met Leu Asp Asn Arg Ala Thr Leu Gln Ala Ile Ala Ser Glu Phe
1               5                   10                  15

Ser Ser Leu Pro
            20

<210> SEQ ID NO 60
<211> LENGTH: 20
<212> TYPE: PRT
<213> ORGANISM: Bovine coronavirus

<400> SEQUENCE: 60

Asp Tyr Ala Lys Asp Asn Thr Val Leu Gln Ala Leu Gln Ser Glu Phe
1               5                   10                  15

Val Asn Met Ala
            20

<210> SEQ ID NO 61
<211> LENGTH: 20
<212> TYPE: PRT
<213> ORGANISM: Human coronavirus

<400> SEQUENCE: 61

Ser Tyr Phe Glu Asn Asp Ser Ile Leu Gln Ser Val Ala Ser Ser Phe
1               5                   10                  15

Val Gly Met Pro
            20

<210> SEQ ID NO 62
<211> LENGTH: 20
<212> TYPE: PRT
<213> ORGANISM: SARS: Human Severe Acute Respiratory Syndrome Virus

<400> SEQUENCE: 62

Leu Arg Ala Asn Ser Ala Val Lys Leu Gln Asn Asn Glu Leu Ser Pro
1               5                   10                  15

Val Ala Leu Arg
            20

<210> SEQ ID NO 63
<211> LENGTH: 20
<212> TYPE: PRT
<213> ORGANISM: Bovine coronavirus

<400> SEQUENCE: 63

His Asn Glu Val Ser Ala Thr Val Leu Gln Asn Asn Glu Leu Met Pro
1               5                   10                  15

Ala Lys Leu Lys
            20

<210> SEQ ID NO 64
<211> LENGTH: 20
<212> TYPE: PRT
<213> ORGANISM: Human coronavirus

<400> SEQUENCE: 64

Leu Thr Cys Glu Arg Val Val Lys Leu Gln Asn Asn Glu Ile Met Pro
1               5                   10                  15

Gly Lys Met Lys
            20
```

```
<210> SEQ ID NO 65
<211> LENGTH: 20
<212> TYPE: PRT
<213> ORGANISM: SARS: Human Severe Acute Respiratory Syndrome Virus

<400> SEQUENCE: 65

Gly Ser Leu Ala Ala Thr Val Arg Leu Gln Ala Gly Asn Ala Thr Glu
1               5                   10                  15

Val Pro Ala Asn
            20

<210> SEQ ID NO 66
<211> LENGTH: 20
<212> TYPE: PRT
<213> ORGANISM: Bovine coronavirus

<400> SEQUENCE: 66

Gly Thr Ile Ser Ser Thr Val Arg Leu Gln Ala Gly Thr Ala Thr Glu
1               5                   10                  15

Tyr Ala Ser Asn
            20

<210> SEQ ID NO 67
<211> LENGTH: 20
<212> TYPE: PRT
<213> ORGANISM: Human coronavirus

<400> SEQUENCE: 67

Gly Tyr Ile Gly Ala Thr Val Arg Leu Gln Ala Gly Lys Gln Thr Glu
1               5                   10                  15

Phe Val Ser Asn
            20

<210> SEQ ID NO 68
<211> LENGTH: 20
<212> TYPE: PRT
<213> ORGANISM: SARS: Human Severe Acute Respiratory Syndrome Virus

<400> SEQUENCE: 68

Cys Asp Gln Leu Arg Glu Pro Leu Met Gln Ser Ala Asp Ala Ser Thr
1               5                   10                  15

Phe Leu Asn Arg
            20

<210> SEQ ID NO 69
<211> LENGTH: 20
<212> TYPE: PRT
<213> ORGANISM: Bovine coronavirus

<400> SEQUENCE: 69

Ser Cys Val Ser Thr Asp Thr Thr Val Gln Ser Lys Asp Thr Asn Phe
1               5                   10                  15

Leu Asn Arg Val
            20

<210> SEQ ID NO 70
<211> LENGTH: 20
<212> TYPE: PRT
<213> ORGANISM: Human coronavirus

<400> SEQUENCE: 70

Gly Cys Thr Cys Asp Arg Thr Ala Ile Gln Ser Phe Asp Asn Ser Tyr
1               5                   10                  15
```

-continued

Leu Asn Arg Val
         20

<210> SEQ ID NO 71
<211> LENGTH: 20
<212> TYPE: PRT
<213> ORGANISM: SARS: Human Severe Acute Respiratory Syndrome Virus

<400> SEQUENCE: 71

Ala Met Tyr Thr Pro His Thr Val Leu Gln Ala Val Gly Ala Cys Val
1               5                   10                  15

Leu Cys Asn Ser
         20

<210> SEQ ID NO 72
<211> LENGTH: 20
<212> TYPE: PRT
<213> ORGANISM: Bovine coronavirus

<400> SEQUENCE: 72

Asn Met Tyr Leu Arg Ser Ala Val Met Gln Ser Val Gly Ala Cys Val
1               5                   10                  15

Val Cys Ser Ser
         20

<210> SEQ ID NO 73
<211> LENGTH: 20
<212> TYPE: PRT
<213> ORGANISM: Human coronavirus

<400> SEQUENCE: 73

Ser Met Tyr Glu Lys Ser Thr Val Leu Gln Ala Ala Gly Leu Cys Val
1               5                   10                  15

Val Cys Gly Ser
         20

<210> SEQ ID NO 74
<211> LENGTH: 20
<212> TYPE: PRT
<213> ORGANISM: SARS: Human Severe Acute Respiratory Syndrome Virus

<400> SEQUENCE: 74

Ile Pro Arg Arg Asn Val Ala Thr Leu Gln Ala Glu Asn Val Thr Gly
1               5                   10                  15

Leu Phe Lys Asp
         20

<210> SEQ ID NO 75
<211> LENGTH: 20
<212> TYPE: PRT
<213> ORGANISM: Bovine coronavirus

<400> SEQUENCE: 75

Val Pro Gln Ala Val Glu Thr Arg Val Gln Cys Ser Thr Asn Leu Phe
1               5                   10                  15

Lys Asp Cys Ser
         20

<210> SEQ ID NO 76
<211> LENGTH: 20
<212> TYPE: PRT
<213> ORGANISM: Human coronavirus

```
<400> SEQUENCE: 76

Phe Phe Glu Ile Thr Met Thr Asp Leu Gln Ser Glu Ser Ser Cys Gly
1               5                   10                  15

Leu Phe Lys Asp
            20

<210> SEQ ID NO 77
<211> LENGTH: 20
<212> TYPE: PRT
<213> ORGANISM: SARS: Human Severe Acute Respiratory Syndrome Virus

<400> SEQUENCE: 77

Asn Leu Trp Asn Thr Phe Thr Arg Leu Gln Ser Leu Glu Asn Val Ala
1               5                   10                  15

Tyr Asn Val Val
            20

<210> SEQ ID NO 78
<211> LENGTH: 20
<212> TYPE: PRT
<213> ORGANISM: Bovine coronavirus

<400> SEQUENCE: 78

Asn Leu Trp Asn Thr Phe Thr Lys Leu Gln Ser Leu Glu Asn Val Val
1               5                   10                  15

Tyr Asn Leu Val
            20

<210> SEQ ID NO 79
<211> LENGTH: 20
<212> TYPE: PRT
<213> ORGANISM: Human coronavirus

<400> SEQUENCE: 79

Trp Gln Thr Phe Thr Glu Val Asn Leu Gln Gly Leu Glu Asn Ile Ala
1               5                   10                  15

Phe Asn Val Val
            20

<210> SEQ ID NO 80
<211> LENGTH: 20
<212> TYPE: PRT
<213> ORGANISM: SARS: Human Severe Acute Respiratory Syndrome Virus

<400> SEQUENCE: 80

His Val Glu Thr Phe Tyr Pro Lys Leu Gln Ala Ser Gln Ala Trp Gln
1               5                   10                  15

Pro Gly Val Ala
            20

<210> SEQ ID NO 81
<211> LENGTH: 20
<212> TYPE: PRT
<213> ORGANISM: Bovine coronavirus

<400> SEQUENCE: 81

Lys Val Met Thr Phe Tyr Pro Arg Leu Gln Ala Ala Ser Asp Trp Lys
1               5                   10                  15

Pro Gly Tyr Ser
            20
```

<210> SEQ ID NO 82
<211> LENGTH: 20
<212> TYPE: PRT
<213> ORGANISM: Human coronavirus

<400> SEQUENCE: 82

Ala Val Ala Thr Phe Tyr Pro Gln Leu Gln Ser Ala Glu Trp Lys Cys
1               5                   10                  15

Gly Tyr Ser Met
            20

<210> SEQ ID NO 83
<211> LENGTH: 9
<212> TYPE: PRT
<213> ORGANISM: Human rhinovirus

<400> SEQUENCE: 83

Arg Pro Val Val Val Gln Gly Pro Asn
1               5

<210> SEQ ID NO 84
<211> LENGTH: 9
<212> TYPE: PRT
<213> ORGANISM: Human coronavirus

<400> SEQUENCE: 84

Ser Thr Leu Gln Ser Gly Leu Arg Lys
1               5

<210> SEQ ID NO 85
<211> LENGTH: 9
<212> TYPE: PRT
<213> ORGANISM: SARS: Human Severe Acute Respiratory Syndrome Virus

<400> SEQUENCE: 85

Ala Thr Val Arg Leu Gln Ala Gly Phe
1               5

<210> SEQ ID NO 86
<211> LENGTH: 16
<212> TYPE: PRT
<213> ORGANISM: SARS: Human Severe Acute Respiratory Syndrome Virus

<400> SEQUENCE: 86

Val Ser Val Asn Ser Thr Leu Gln Ser Gly Leu Arg Lys Met Ala Cys
1               5                   10                  15

<210> SEQ ID NO 87
<211> LENGTH: 12
<212> TYPE: PRT
<213> ORGANISM: Human rhinovirus 14

<400> SEQUENCE: 87

Lys Ser Ile Val Pro Gln Gly Leu Pro Thr Thr Thr
1               5                   10

<210> SEQ ID NO 88
<211> LENGTH: 12
<212> TYPE: PRT
<213> ORGANISM: Human rhinovirus 14

<400> SEQUENCE: 88

Cys Ile Ala Glu Glu Gln Gly Leu Ser Asp Tyr Ile
1               5                   10

<210> SEQ ID NO 89
<211> LENGTH: 12
<212> TYPE: PRT
<213> ORGANISM: Human rhinovirus 14

<400> SEQUENCE: 89

Leu Glu Thr Leu Phe Gln Gly Pro Val Tyr Lys Asp
1               5                   10

<210> SEQ ID NO 90
<211> LENGTH: 12
<212> TYPE: PRT
<213> ORGANISM: Human rhinovirus 14

<400> SEQUENCE: 90

Leu Phe Ala Gln Thr Gln Gly Pro Tyr Ser Gly Asn
1               5                   10

<210> SEQ ID NO 91
<211> LENGTH: 12
<212> TYPE: PRT
<213> ORGANISM: Human rhinovirus 14

<400> SEQUENCE: 91

Arg Pro Val Val Val Gln Gly Pro Asn Thr Glu Phe
1               5                   10

<210> SEQ ID NO 92
<211> LENGTH: 12
<212> TYPE: PRT
<213> ORGANISM: Human rhinovirus 14

<400> SEQUENCE: 92

Gly Gly Asn Gly Arg Gln Gly Phe Ser Ala Gln Leu
1               5                   10

<210> SEQ ID NO 93
<211> LENGTH: 12
<212> TYPE: PRT
<213> ORGANISM: Human rhinovirus 14

<400> SEQUENCE: 93

Tyr Phe Val Glu Lys Gln Gly Gln Val Ile Ala Arg
1               5                   10

<210> SEQ ID NO 94
<211> LENGTH: 12
<212> TYPE: PRT
<213> ORGANISM: Human rhinovirus 14

<400> SEQUENCE: 94

Ser Asn Leu Val Val Gln Ala Met Tyr Val Pro His
1               5                   10

<210> SEQ ID NO 95
<211> LENGTH: 12
<212> TYPE: PRT
<213> ORGANISM: Human rhinovirus 14

<400> SEQUENCE: 95

Tyr Pro Ser Arg Phe Gln Ala Gly Val Met Lys Gly
1               5                   10

<210> SEQ ID NO 96
<211> LENGTH: 12
<212> TYPE: PRT
<213> ORGANISM: Human rhinovirus 14

<400> SEQUENCE: 96

Pro Tyr Ile Glu Arg Gln Ala Asn Asp Gly Trp Phe
1               5                   10

<210> SEQ ID NO 97
<211> LENGTH: 12
<212> TYPE: PRT
<213> ORGANISM: Human rhinovirus 14

<400> SEQUENCE: 97

Asn Lys Val Leu Pro Gln Ala Lys Glu Lys Leu Glu
1               5                   10

<210> SEQ ID NO 98
<211> LENGTH: 12
<212> TYPE: PRT
<213> ORGANISM: Human rhinovirus 14

<400> SEQUENCE: 98

Glu Arg Ala Met Asn Gln Ala Ser Met Ile Ile Asn
1               5                   10

<210> SEQ ID NO 99
<211> LENGTH: 12
<212> TYPE: PRT
<213> ORGANISM: Human rhinovirus 14

<400> SEQUENCE: 99

Gln Leu Ala Ser His Glu Gly Gly Asn Val Ser Val
1               5                   10

<210> SEQ ID NO 100
<211> LENGTH: 12
<212> TYPE: PRT
<213> ORGANISM: Human rhinovirus 14

<400> SEQUENCE: 100

Thr Val Ala Leu Thr Glu Gly Leu Gly Asp Glu Leu
1               5                   10

<210> SEQ ID NO 101
<211> LENGTH: 12
<212> TYPE: PRT
<213> ORGANISM: Human rhinovirus 14

<400> SEQUENCE: 101

Thr Asn Ile Trp Ile Glu Gly Ser Pro Tyr Tyr Pro
1               5                   10

<210> SEQ ID NO 102
<211> LENGTH: 12
<212> TYPE: PRT
<213> ORGANISM: Human rhinovirus 14

<400> SEQUENCE: 102

Gly Leu Leu Thr Ala Glu Gly Ser Gly Tyr Val Cys
1               5                   10

<210> SEQ ID NO 103
<211> LENGTH: 12

```
<212> TYPE: PRT
<213> ORGANISM: Human rhinovirus 14

<400> SEQUENCE: 103

Ile Ser Glu Asp Leu Glu Gly Val Asp Ala Thr Leu
1               5                   10

<210> SEQ ID NO 104
<211> LENGTH: 12
<212> TYPE: PRT
<213> ORGANISM: Human rhinovirus 14

<400> SEQUENCE: 104

Glu Ile Tyr Val Val Glu Gly Gly Met Pro Ser Gly
1               5                   10

<210> SEQ ID NO 105
<211> LENGTH: 13
<212> TYPE: PRT
<213> ORGANISM: Human rhinovirus 14

<400> SEQUENCE: 105

Asp Ser Leu Glu Thr Leu Phe Gln Gly Pro Val Tyr Lys
1               5                   10

<210> SEQ ID NO 106
<211> LENGTH: 14
<212> TYPE: PRT
<213> ORGANISM: Human rhinovirus 14

<400> SEQUENCE: 106

Glu Ala Ile Ala Glu Glu Gln Gly Leu Ser Asp Tyr Ile Thr
1               5                   10

<210> SEQ ID NO 107
<211> LENGTH: 15
<212> TYPE: PRT
<213> ORGANISM: Human rhinovirus 14

<400> SEQUENCE: 107

Val Pro Tyr Ile Glu Arg Gln Ala Asn Asp Gly Trp Phe Arg Lys
1               5                   10                  15

<210> SEQ ID NO 108
<211> LENGTH: 15
<212> TYPE: PRT
<213> ORGANISM: Human rhinovirus 14

<400> SEQUENCE: 108

Arg Ser Lys Ser Ile Val Pro Gln Gly Leu Pro Thr Thr Thr Tyr
1               5                   10                  15

<210> SEQ ID NO 109
<211> LENGTH: 17
<212> TYPE: PRT
<213> ORGANISM: Human rhinovirus 14

<400> SEQUENCE: 109

Ser Gln Thr Val Ala Leu Thr Glu Gly Leu Gly Asp Glu Leu Glu Glu
1               5                   10                  15

Tyr

<210> SEQ ID NO 110
<211> LENGTH: 14
```

-continued

<212> TYPE: PRT
<213> ORGANISM: Human rhinovirus 14

<400> SEQUENCE: 110

Lys Leu Phe Ala Gln Thr Gln Gly Pro Tyr Ser Gly Asn Pro
1 5 10

<210> SEQ ID NO 111
<211> LENGTH: 13
<212> TYPE: PRT
<213> ORGANISM: Human rhinovirus 14

<400> SEQUENCE: 111

Tyr Arg Pro Val Val Val Gln Gly Pro Asn Thr Glu Phe
1 5 10

<210> SEQ ID NO 112
<211> LENGTH: 14
<212> TYPE: PRT
<213> ORGANISM: Human rhinovirus 14

<400> SEQUENCE: 112

Lys Gln Tyr Phe Val Glu Lys Gln Gly Gln Val Ile Ala Arg
1 5 10

<210> SEQ ID NO 113
<211> LENGTH: 10
<212> TYPE: PRT
<213> ORGANISM: Human rhinovirus 1A
<220> FEATURE:
<221> NAME/KEY: MISC_FEATURE
<223> OTHER INFORMATION: MOC; fluorochrome
<220> FEATURE:
<221> NAME/KEY: MISC_FEATURE
<222> LOCATION: (10)..()
<223> OTHER INFORMATION: DNP-NH2; Dinitrophenol quencher

<400> SEQUENCE: 113

Arg Ala Glu Leu Gln Gly Pro Tyr Asp Lys
1 5 10

<210> SEQ ID NO 114
<211> LENGTH: 19
<212> TYPE: PRT
<213> ORGANISM: Human Poliovirus- POLIM

<400> SEQUENCE: 114

Ile Gly Asn Cys Met Glu Ala Leu Phe Gln Gly Pro Gln Tyr Lys Asp
1 5 10 15

Leu Lys Ile

<210> SEQ ID NO 115
<211> LENGTH: 20
<212> TYPE: PRT
<213> ORGANISM: Human Poliovirus- POLIS

<400> SEQUENCE: 115

Ile Gly Asn Cys Met Glu Ala Leu Phe Gln Gly Pro Leu Gln Tyr Lys
1 5 10 15

Asp Leu Lys Ile
20

<210> SEQ ID NO 116
<211> LENGTH: 20
<212> TYPE: PRT

<213> ORGANISM: Human Poliovirus- POL32

<400> SEQUENCE: 116

Ile Gly Asn Cys Met Glu

<210> SEQ ID NO 122
<211> LENGTH: 20
<212> TYPE: PRT
<213> ORGANISM: Human Coxacivirus -COXB1

<400> SEQUENCE: 122

Val Gly Ala Thr Leu Glu Ala Leu Phe Gln Gly Pro Pro Ile Tyr Arg
1               5                   10                  15

Glu Ile Lys Ile
            20

<210> SEQ ID NO 123
<211> LENGTH: 20
<212> TYPE: PRT
<213> ORGANISM: Human Coxacivirus -COXB5

<400> SEQUENCE: 123

Val Gly Ala Thr Leu Glu Ala Leu Phe Gln Gly Pro Pro Ile Tyr Arg
1               5                   10                  15

Glu Ile Lys Ile
            20

<210> SEQ ID NO 124
<211> LENGTH: 20
<212> TYPE: PRT
<213> ORGANISM: Human Echovirus  EC11G

<400> SEQUENCE: 124

Val Gly Ala Thr Leu Glu Ala Leu Phe Gln Gly Pro Pro Ile Tyr Arg
1               5                   10                  15

Glu Ile Lys Ile
            20

<210> SEQ ID NO 125
<211> LENGTH: 20
<212> TYPE: PRT
<213> ORGANISM: Human Coxacivirus -COXB4

<400> SEQUENCE: 125

Val Gly Ala Thr Leu Glu Ala Leu Phe Gln Gly Pro Pro Val Tyr Arg
1               5                   10                  15

Glu Ile Lys Ile
            20

<210> SEQ ID NO 126
<211> LENGTH: 20
<212> TYPE: PRT
<213> ORGANISM: Swine Vesicular Disease Virus SVDVH

<400> SEQUENCE: 126

Val Gly Ala Thr Leu Glu Ala Leu Phe Gln Gly Pro Pro Val Tyr Arg
1               5                   10                  15

Glu Ile Lys Ile
            20

<210> SEQ ID NO 127
<211> LENGTH: 20
<212> TYPE: PRT
<213> ORGANISM: Swine Vesicular Disease Virus SVDVU

<400> SEQUENCE: 127

-continued

```
Val Gly Ala Thr Leu Glu Ala Leu Phe Gln Gly Pro Pro Val Tyr Arg
1               5                   10                  15

Glu Ile Lys Ile
            20

<210> SEQ ID NO 128
<211> LENGTH: 20
<212> TYPE: PRT
<213> ORGANISM: Human Coxacivirus -COXB3

<400> SEQUENCE: 128

Val Gly Thr Thr Leu Glu Ala Leu Phe Gln Gly Pro Pro Val Tyr Arg
1               5                   10                  15

Glu Ile Lys Ile
            20

<210> SEQ ID NO 129
<211> LENGTH: 20
<212> TYPE: PRT
<213> ORGANISM: Human Enterovirus HUEV7

<400> SEQUENCE: 129

Thr Gln Asp Lys Leu Glu Ala Leu Phe Gln Gly Pro Pro Thr Phe Lys
1               5                   10                  15

Glu Ile Lys Ile
            20

<210> SEQ ID NO 130
<211> LENGTH: 20
<212> TYPE: PRT
<213> ORGANISM: Human rhinovirus 1B

<400> SEQUENCE: 130

Val Val Asp Val Met Ser Ala Ile Phe Gln Gly Pro Ile Ser Leu Asp
1               5                   10                  15

Ala Pro Pro Pro
            20

<210> SEQ ID NO 131
<211> LENGTH: 20
<212> TYPE: PRT
<213> ORGANISM: Human rhinovirus 2

<400> SEQUENCE: 131

Val Val Asp Val Met Thr Ala Ile Phe Gln Gly Pro Ile Asp Met Lys
1               5                   10                  15

Asn Pro Pro Pro
            20

<210> SEQ ID NO 132
<211> LENGTH: 20
<212> TYPE: PRT
<213> ORGANISM: Human rhinovirus 89

<400> SEQUENCE: 132

Ala Ala Gln Ala Met Glu Ala Ile Phe Gln Gly Ile Asp Leu Gln Ser
1               5                   10                  15

Pro Pro Pro Pro
            20

<210> SEQ ID NO 133
<211> LENGTH: 20
```

```
<212> TYPE: PRT
<213> ORGANISM: Human rhinovirus 14

<400> SEQUENCE: 133

Ile Thr Asp Ser Leu Glu Thr Leu Phe Gln Gly Pro Val Tyr Lys Asp
1               5                   10                  15

Leu Glu Ile Asp
            20
```